(12) United States Patent
Scalone et al.

(10) Patent No.: US 8,106,187 B2
(45) Date of Patent: Jan. 31, 2012

(54) PROCESS FOR THE PREPARATION OF A MACROCYCLE

(75) Inventors: Michelangelo Scalone, Birsfelden (CH); Helmut Stahr, Loerrach (DE)

(73) Assignee: Roche Palo Alto LLC, South San Francisco, CA (US)

( * ) Notice: Subject to any disclaimer, the term of this patent is extended or adjusted under 35 U.S.C. 154(b) by 371 days.

(21) Appl. No.: 12/462,736

(22) Filed: Aug. 7, 2009

(65) Prior Publication Data

US 2010/0036116 A1 Feb. 11, 2010

(30) Foreign Application Priority Data

Aug. 7, 2008 (EP) ..................................... 08162026

(51) Int. Cl.
C07D 403/12 (2006.01)
C07D 487/04 (2006.01)
(52) U.S. Cl. ...................................... 540/460; 548/465
(58) Field of Classification Search .................. 540/460; 548/465
See application file for complete search history.

(56) References Cited

U.S. PATENT DOCUMENTS
2005/0267018 A1 12/2005 Blatt et al.
2007/0054842 A1 3/2007 Blatt et al.

FOREIGN PATENT DOCUMENTS
WO 2008086161 A1 7/2008
WO 2009070692 A1 6/2009
WO 2009080542 A1 7/2009

*Primary Examiner* — Bruck Kifle
(74) *Attorney, Agent, or Firm* — Brian L. Buckwalter

(57) ABSTRACT

The present invention relates to a new process for the preparation of macrocyclic HCV protease inhibitor compounds of the formula

XXII wherein $R^1$ is an amino protecting group and X is halogen by way of a ring closing metathesis approach.

24 Claims, No Drawings

PROCESS FOR THE PREPARATION OF A MACROCYCLE

CROSS REFERENCE TO PRIOR APPLICATIONS

This application claims the benefit of priority to EP 08162026.2 filed Aug. 7, 2008 the contents of which are hereby incorporated in their entirety by reference.

FIELD OF THE INVENTION

The present invention relates to a new process for the preparation of macrocyclic HCV protease inhibitors of the formula XXII wherein $R^1$ is an amino protecting group and X is halogen. One object of the present invention is an improved process which is applicable on technical scale and which overcomes the disadvantages known in the art.

BACKGROUND OF THE INVENTION

The HCV protease inhibitor compound of the formula XXIIb has entered clinical development.

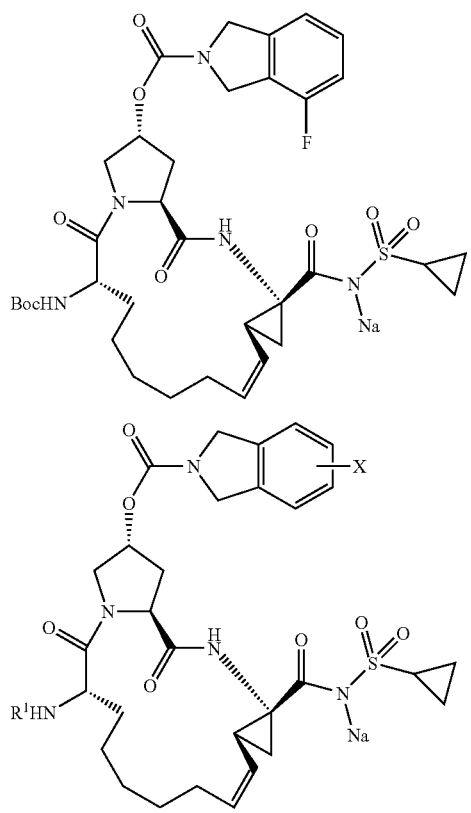

XXIIb

XXII

The key step in the synthesis of the macrocyclic compounds of formula XXII is a ring closing metathesis (RCM) reaction of a diene compound in the presence of a suitable ring closing metathesis catalyst.

PCT Publication WO 2005/037214 and PCT Publication WO 2007/015824 disclose the RCM of a diene compound of the formula 2a in the presence of a Nolan or Hoveyda catalyst to afford the macrocyclic ester of formula 2b.

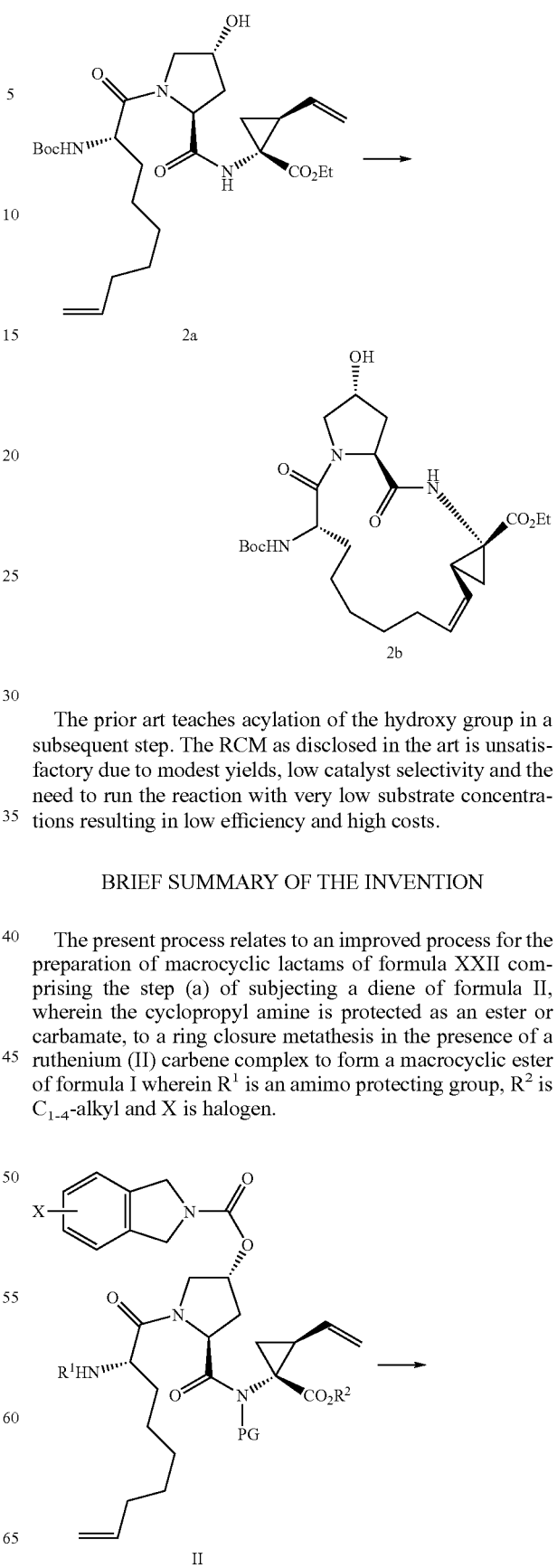

2a

2b

The prior art teaches acylation of the hydroxy group in a subsequent step. The RCM as disclosed in the art is unsatisfactory due to modest yields, low catalyst selectivity and the need to run the reaction with very low substrate concentrations resulting in low efficiency and high costs.

BRIEF SUMMARY OF THE INVENTION

The present process relates to an improved process for the preparation of macrocyclic lactams of formula XXII comprising the step (a) of subjecting a diene of formula II, wherein the cyclopropyl amine is protected as an ester or carbamate, to a ring closure metathesis in the presence of a ruthenium (II) carbene complex to form a macrocyclic ester of formula I wherein $R^1$ is an amimo protecting group, $R^2$ is $C_{1-4}$-alkyl and X is halogen.

II

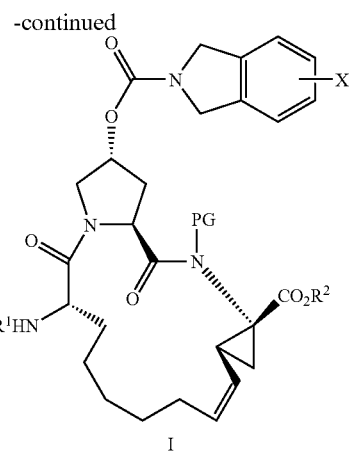

I

The process further comprises steps to transform I to the macrocyclic acyl sulfonamide XXII. In addition the present invention provides novel synthetic intermediates which can be utilized advantageously to prepare compounds of formula XXII.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The following definitions are set forth to illustrate and define the meaning and scope of the various terms used to describe the invention herein.

The term "amino protecting group" refers to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. Suitable amino protecting groups for $R^1$ are Fmoc, Cbz, Moz, Boc, Troc, Teoc or Voc. Preferred amino protecting group, as defined for $R^1$ is Boc. Suitable amino protecting group for PG is $C_{1-6}$-alkylcarbonyl, arylcarbonyl or $C_{1-6}$-alkoxycarbonyl, but preferably benzoyl.

The term "halogen" refers to fluorine, chlorine, bromine and iodine. The preferred halogen as a rule is chlorine, while the preferred halogen for X is fluorine.

In one embodiment of the present invention there is provided a process to prepare compounds of formula I, II, XX, XXI and XXII where the moiety XXIVa is XXIVb:

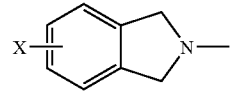

XXIVa

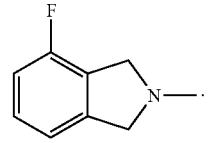

XXIVb

The term "$C_{1-6}$-alkyl", alone or in combination with other groups, refers to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl and pentyl or hexyl and its isomers.

The term "$C_{1-4}$-alkyl" as used in herein for $R^2$ refers to a branched or straight-chain monovalent saturated aliphatic hydrocarbon radical of one to four carbon atoms such as methyl, ethyl, n-propyl, isopropyl, n-butyl, s-butyl, t-butyl, preferably to ethyl.

The term "$C_{2-6}$-alkenyl", alone or in combination with other groups, refers to a branched or straight-chain monovalent unsaturated aliphatic hydrocarbon radical of two to six carbon atoms, preferably two to four carbon atoms. This term is further exemplified by radicals as vinyl, propenyl, butenyl, pentenyl and hexenyl and their isomers. A preferred alkenyl radical is vinyl.

The term "$C_{2-6}$-alkynyl", alone or in combination with other groups, refers to a branched or straight-chain monovalent unsaturated aliphatic hydrocarbon radical of two to six carbon atoms, preferably two to four carbon atoms. This term is further exemplified by radicals as ethynyl, propynyl, butynyl, pentynyl or hexynyl their isomers.

The term "$C_{1-6}$ haloalkyl" refers to a halogen substituted $C_{1-6}$-alkyl radical wherein halogen has the meaning as above. Preferred "$C_{1-6}$ haloalkyl" radicals include the fluorinated $C_{1-6}$-alkyl radicals such as $CF_3$, $CH_2CF_3$, $CH(CF_3)_2$, $CH(CH_3)(CF_3)$, $C_4F_9$.

The term "$C_{1-6}$-alkoxy" refers to a branched or straight-chain monovalent saturated aliphatic hydrocarbon radical of one to six carbon atoms, preferably 1 to 4 carbon atoms attached to an oxygen atom. Examples of "alkoxy" are methoxy, ethoxy, propoxy, isopropoxy, butoxy, isobutoxy, tert-butoxy and hexyloxy. Preferred are the alkoxy groups specifically exemplified herein.

The alkyl chain of the alkoxy group can optionally be substituted, particularly mono-, di- or tri-substituted by alkoxy groups as defined above, preferably methoxy, or ethoxy or by aryl groups, preferably phenyl. A Preferred substituted alkoxy group is the benzyloxy group.

The term "$C_{1-6}$-alkyl carbonyl" refers to $C_{1-6}$-alkyl substituted carbonyl group, preferably to a $C_{1-4}$-alkylcarbonyl group. It includes for example acetyl, propanoyl, butanoyl or pivaloyl. A preferred alkyl carbonyl group is acetyl.

The term "$C_{1-6}$-alkylthio" refers to the group $C_{1-6}$-alkyl-S—, preferably $C_{1-4}$-alkyl e.g. methylthio or ethylthio. Preferred are the alkylthio groups specifically exemplified herein.

The term "arylthio" refers to a group aryl-S—, preferably to phenylthio.

The term "$C_{1-6}$-alkylsulfonyl" refers to a $C_{1-6}$-alkyl substituted sulfonyl group, preferably to methylsulfonyl.

The term "$C_{1-6}$-alkylsulfinyl" refers to a $C_{1-6}$-alkyl substituted sulfinyl group, preferably to methylsulfinyl.

The term "$SO_2$-aryl" refers to a sulfonyl substituted aryl radical. Preferred $SO_2$-aryl radical is $SO_2$-phenyl.

The term "$SO_2$—NR'R" refers to a sulfonyl group substituted with an amino group NR'R" wherein R' and R" are (i) independently hydrogen or $C_{1-6}$-alkyl or (ii) R' and R" together with the N atom to which they are attached form a carbocycle, e.g. —$(CH_2)_4$— or —$(CH)_4$—. A preferred $SO_2$—NR'R" radical is $SO_2$—$N(CH_3)_2$.

The term "mono- or di-$C_{1-6}$-alkyl-amino" refers to an amino group, which is mono- or disubstituted with $C_{1-6}$-alkyl, preferably $C_{1-4}$-alkyl. A mono-$C_{1-6}$-alkyl-amino group includes for example methylamino or ethylamino. The term "di-$C_{1-6}$-alkyl-amino" includes for example dimethylamino, diethylamino or ethylmethylamino. Preferred are the mono- or di-$C_{1-4}$-alkylamino groups specifically exemplified herein. It is hereby understood that the term "di-$C_{1-6}$-alkyl-amino" includes ring systems wherein the two alkyl groups together with the nitrogen atom to which they are attached form a 4 to 7 membered heterocycle which also contain one further hetero atom selected from nitrogen, oxygen or sulfur.

The term "cycloalkyl" denotes a "$C_{3-7}$-cycloalkyl" group containing from 3 to 7 carbon atoms, such as cyclopropyl, cyclobutyl, cyclopentyl, cyclohexyl or cycloheptyl.

The term "aryl" relates to the phenyl or naphthyl group, which can optionally be mono-, di-, tri- or multiply-substituted by halogen, hydroxy, CN, $C_{1-6}$ haloalkyl, $NO_2$, $NH_2$, N(H,alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R", aryl and/or aryloxy. A preferred aryl group usually is phenyl, however the preference for aryl may differ as indicated hereinafter for certain substituents.

The term "aryloxy" relates to an aryl radical attached to an oxygen atom. The term "aryl" has the meaning as defined above. A preferred aryloxy group is phenyloxy.

The term "arylalkyl" relates to an aryl radical attached to an alkyl group. The term "aryl" has the meaning as defined above. A preferred arylalkyl group is benzyl.

The term "arylcarbonyl" relates to an aryl radical attached to a carbonyl group. The term "aryl" has the meaning as defined above. A preferred arylcarbonyl group is benzoyl.

The term "heteroaryl" relates to a heterocyclic aryl radical containing 1 to 3 heteroatoms in the ring with the remainder being carbon atoms. Suitable heteroatoms include, without limitation, oxygen, sulfur, and nitrogen. Exemplary heteroaryl groups include furanyl, thienyl, pyridyl, pyrrolyl, N-alkyl pyrrolo, pyrimidyl, pyrazinyl, imidazolyl, benzofuranyl, quinolinyl, and indolyl. Like the heteroaryl group can optionally be mono-, di-, tri- or multiply-substituted by halogen, hydroxy, CN, $NO_2$, $NH_2$, N(H,alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R", aryl and/or aryloxy.

In one embodiment of the present invention there is provided a process for the manufacture of a macrocyclic compound of formula XXII wherein $R^1$ is an amino protecting group and X is a halogen atom, comprising the step (a) of subjecting a diene compound of

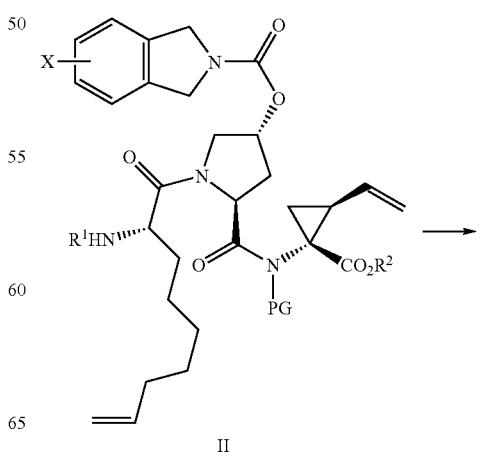

II

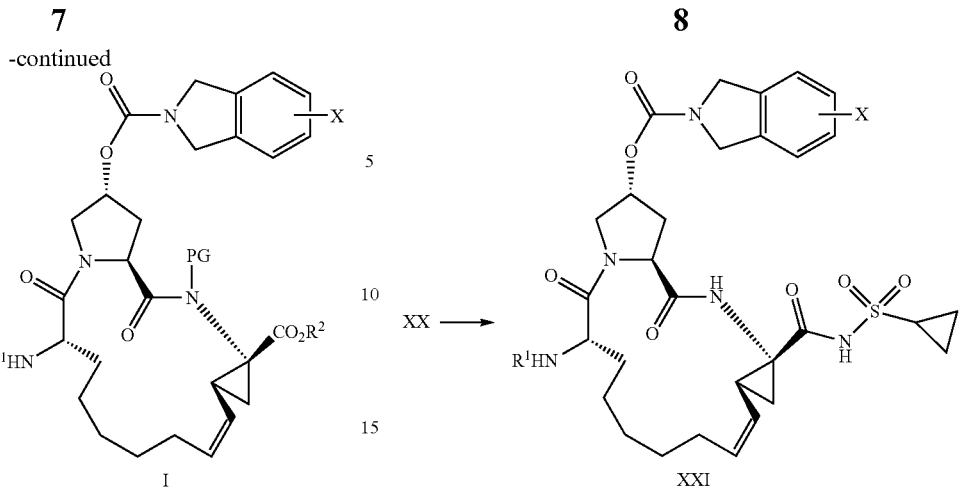

formula II wherein $R^1$ and PG are amino protecting groups, $R^2$ is $C_{1-4}$-alkyl and is X is halogen to an RCM in the presence of a ruthenium (II) carbene complex catalyst to form a macrocyclic ester of the formula I wherein $R^1$ and PG are amino protecting groups, $R^2$ is $C_{1-4}$-alkyl and X is halogen.

In a second embodiment of the present invention there is provided a process for the manufacture of a macrocyclic compound of formula XXII wherein $R^1$ is an amino protecting group and X is a halogen atom comprising the steps of:

(a) of subjecting a diene compound of formula II wherein $R^1$ and PG are amino protecting groups, $R^2$ is $C_{1-4}$-alkyl and is X is halogen to a ring closing metathesis reaction in the presence of a ruthenium (II) carbene complex catalyst to form a macrocyclic ester of the formula I wherein $R^1$ and PG are amino protecting groups, $R^2$ is $C_{1-4}$-alkyl and X is halogen;

(b) hydrolyzing the macrocyclic ester of formula I and concomitantly removing the protecting group PG to afford the macrocyclic acid of the formula XX wherein $R^1$ is an amino protecting group and X is halogen;

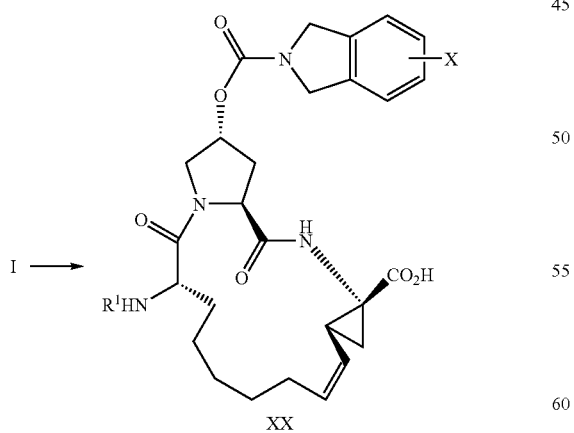

(c) condensing the macrocyclic acid of formula XX wherein $R^1$ is an amino protecting group and X is halogen and cyclopropyl sulfonamide to produce the macrocyclic sulfonamide of formula XXI; and, (d) treating the macrocyclic sulfonamide of formula XXI with a sodium base to form a sodium salt of the macrocyclic compound of formula XXII.

The diene starting compound of formula XV can be prepared as depicted in SCHEME 1.

SCHEME 1

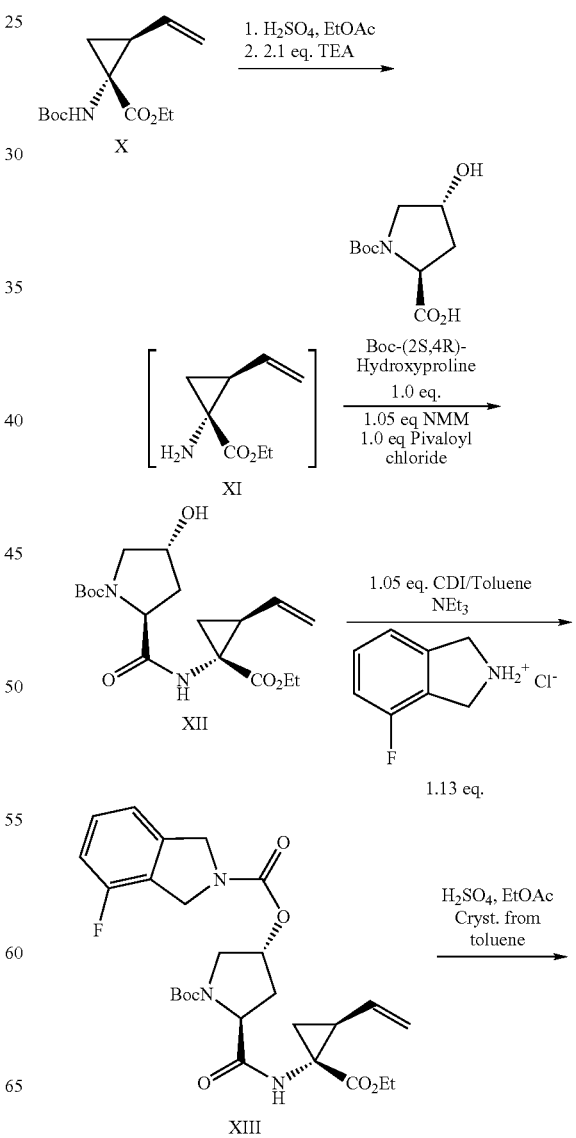

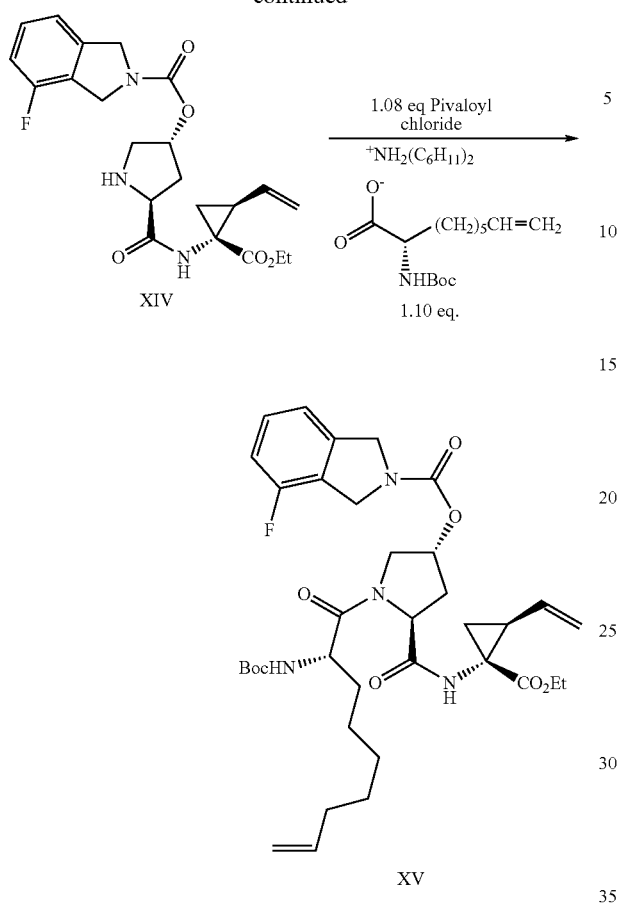

For example the vinylcyclopropanecarboxylate X is treated with sulfuric acid to form XI, which is then coupled with Boc-(2S,4R)-hydroxyproline to form XII. Carbamoylation of the free OH group with carbonyl diimidazole and 4-fluoroisoindoline leads to XIII and removal of the Boc-protecting group and addition of the (S)-2-tert-butoxycarbonylamino-non-8-enoic acid side chain affords the diene XV.

SCHEME 2

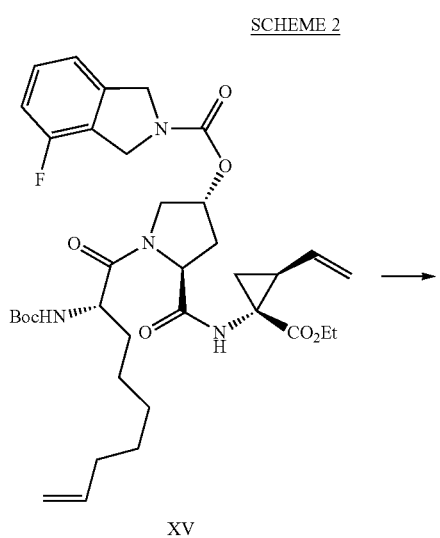

XV

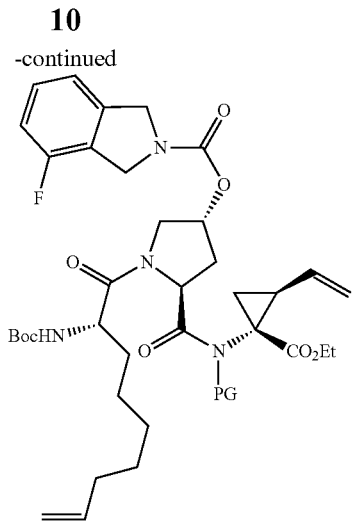

II a: PG = Me$_3$COC(=O) (conditions a)
II b: PG = MeC(=O) (conditions b)
II c: PG = EtC(=O) (conditions c)
II d: PG = PhC(=O) (conditions d)

(a) Boc$_2$O, DMAP (0.3 Eq), THF, rt;
(b) Ac$_2$O (2.5-3 Eq), LiCl, NEt$_3$; THF, 67° C.;
(c) (EtCO)$_2$O, LiCl (3 Eq), NEt$_3$, THF, 80° C.;
(d) PhCOCl, LiOtBu (1.5-2 Eq), toluene, -3° C.

The introduction of the N-substitution to afford the diene of formula II can be accomplished according to SCHEME 2. For example diene XV is treated with a carboxylic acid anhydride in the presence of an alkali or alkali earth halogenide such as lithium chloride to introduce C$_{1-6}$-alkylcarbonyl substituents like acetyl or with a dialkyl dicarbonate or an alkyl chloroformate in the presence of a base such as with 4-dimethylamino-pyridine to introduce C$_{1-6}$-alkoxycarbonyl substituents like Boc.

In another embodiment of the present invention there is provided a compound according to formula II wherein R$^1$ and PG are amino protecting groups, R$^2$ is C$_{1-4}$-alkyl and is X is halogen.

II

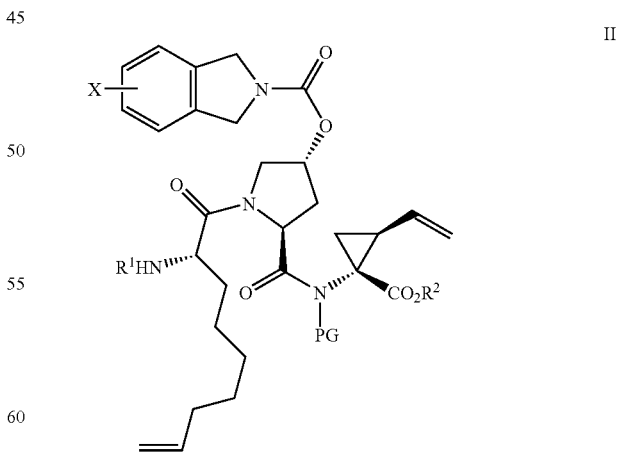

In another embodiment of the present invention there is provided a compound according to formula II wherein R$^1$ is Boc, R$^2$ is ethyl, PG is C$_{1-6}$-alkylcarbonyl, arylcarbonyl or C$_{1-6}$-alkoxycarbonyl and the moiety XXIVa is XXIVb.

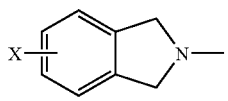

XXIVa

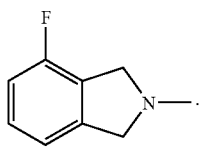

XXIVb

In another embodiment of the present invention there is provided a compound according to formula II wherein $R^1$ is Boc, $R^2$ is ethyl; PG is benzoyl and the moiety XXIVa is XXIVb.

In another embodiment of the present invention there is provided a compound according to formula I wherein $R^1$ and PG are amino protecting groups, $R^2$ is $C_{1-4}$-alkyl, the moiety XXIVa is XXIVa and is X is halogen.

In another embodiment of the present invention there is provided a compound according to formula I wherein $R^1$ is Boc, $R^2$ is ethyl; PG is benzoyl and the moiety XXIVa is XXIVb.

In another embodiment of the present invention there is provided a process comprising steps (a) to (d) wherein the RCM catalyst for the ring closing of the diene in step (a) is selected from the group consisting of IIIa, IIIb, IIIc, IIId, IIIe, IIIf, IIIg and IIIh.

IIIa

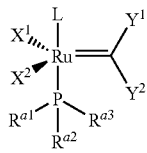

IIIb

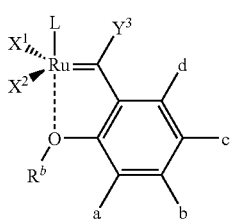

IIIc

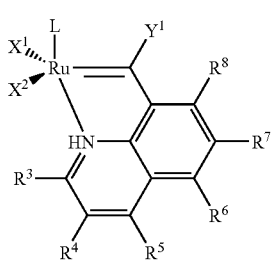

IIId

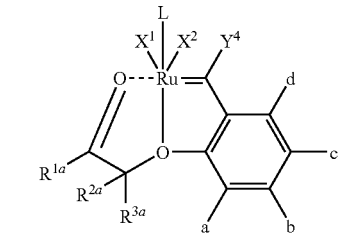

IIIe

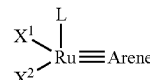

IIIf

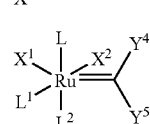

IIIg

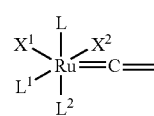

IIIh

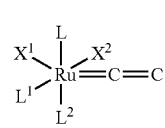

L, $L^1$ and $L^2$ are neutral ligands;

$X^1$ and $X^2$ are independently anionic ligands;

$Y^1$ and $Y^2$ (i) independently of each other are hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl, or (ii) $Y^1$ and $Y^2$ taken together with the carbon atom to which they are attached form a carbocycle VIa wherein G is hydrogen or aryl or (iii) $Y^1$ and $Y^2$ taken together with the carbon atom to which they are attached form a cumulene VIb or VIc.

VIa

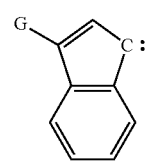

VIb

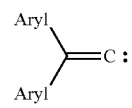

VIc

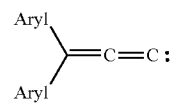

$Y^3$ is hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl.

$Y^4$ and $Y^5$ independently of each other are hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl or $C_{1-6}$-alkylsulfinyl.

$R^{a1}$, $R^{a2}$ and $R^{a3}$ are (i) independently $C_{1-6}$-alkyl, $C_{3-7}$-cycloalkyl, aryl, heteroaryl or (ii) $R^{a1}$ and $R^{a2}$ or $R^{a2}$ and $R^{a3}$ or $R^{a1}$ and $R^{a3}$ form together a 1,5-bridged cyclooctyl group.

$R^b$ is $C_{1-6}$-alkyl, $C_{2-6}$-alkenyl, halogen-$C_{1-6}$-alkyl, $C_{2-6}$-alkynyl, aryl, $C_{1-6}$-alkoxycarbonyl, $C_{1-6}$-alkylcarbonyl, mono-$C_{1-6}$-alkyl- or di-$C_{1-6}$-alkylamino, $C_{1-6}$-alkylaminocarbonyl, $C_{1-6}$-alkylthiocarbonyl, $C_{1-6}$-alkylsulfonyl, $C_{1-6}$-alkylsulfinyl or arylalkyl.

$R^3$, $R^4$, $R^5$, $R^6$, $R^7$ and $R^8$ are independently hydrogen, $C_{1-6}$-alkyl, $C_{1-6}$ haloalkyl, $C_{2-6}$-alkenyl, $C_{2-6}$-alkynyl, $C_{1-6}$ haloalkyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$ haloalkyl sulfonyl amino, $SO_3$—$C_{1-6}$-alkyl or $OSi(C_{1-6}$-alkyl$)_3$ and $SO_2$—NR'R" wherein R' and R" (i) independently are hydrogen, aryl or $C_{1-6}$-alkyl or (ii) R' and R" together with the N atom to which they are attached form a carbocycle.

a, b, c and d are independently hydrogen, $C_{1-6}$-alkyl, $C_{1-6}$ haloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$-haloalkyl sulfonyl amino, $SO_3$—$C_{1-6}$-alkyl, $OSi(C_{1-6}$-alkyl$)_3$ or $SO_2$—NR'R" wherein (i) R' and R" are independently hydrogen, aryl or $C_{1-6}$-alkyl, or (ii) R' and R" together with the N atom to which they are attached form a carbocycle.

Arene stands for phenyl or naphthyl optionally mono-, di-, tri- or multiply-substituted by halogen, hydroxy, cyano, $C_{1-6}$-haloalkyl, $NO_2$, amino, mono-$C_{1-6}$-alkyl- or di-$C_{1-6}$-alkylamino, carboxy, aminocarbonyl, $C_{1-6}$-alkyl, $C_{1-6}$-alkoxy, $C_{1-6}$-alkylcarbonyl, $C_{1-6}$-alkylsulfonyl, aryl, aryloxy $SO_2$-aryl, $SO_3H$, $SO_3$—$C_{1-6}$-alkyl or $SO_2$—NR'R" wherein R' and R" independently of each other are hydrogen or $C_{1-6}$-alkyl.

$R^{1a}$ is hydrogen, hydroxy, $C_{1-6}$-alkyl, $C_{1-6}$-alkoxy, $C_{2-6}$-alkenyloxy, $C_{3-8}$-cycloalkyloxy, halogen-$C_{1-6}$-alkyloxy, aryl, aryloxy, $C_{1-6}$-alkylthio, arylthio, or —NR'R" wherein (i) R' and R" are independently hydrogen, $C_{1-6}$-alkyl, $C_{3-8}$-cycloalkyl, aryl or aryl-$C_{1-6}$-alkyl or (ii) R' and R" together with the N atom to which they are attached form a 5 to 8 member carbocycle which may contain nitrogen, oxygen or sulfur as additional hetero atom.

$R^{2a}$ and $R^{3a}$ are (i) independently of each other hydrogen, $C_{1-6}$-alkyl, $C_{3-8}$-cycloalkyl, aryl or $C_{7-18}$-arylalkyl, or, (ii) $R^{1a}$ and $R^{2a}$ or $R^{3a}$ together form a 5 to 12 member carbocycle.

In another embodiment of the present invention there is provided a process comprising steps (a) to (d) wherein the RCM catalyst for the ring closing of the diene in step (a) is selected from the group consisting of IIIa, IIIb, IIIc, IIId, IIIe, IIIf, IIIg and IIIh wherein L

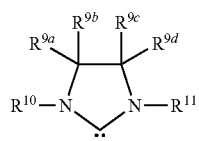

VII

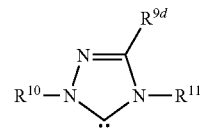

VIII

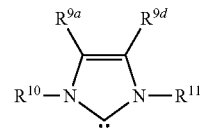

IX

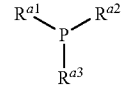

XVII is a neutral ligand preferably selected from VII, VIII, IX or XVII and $R^{10}$ and $R^{11}$ are independently $C_{1-6}$-alkyl, aryl, $C_{2-6}$-alkenyl or 1-adamantyl.

$R^{9a-d}$ are (i) independently hydrogen, $C_{1-6}$-alkyl, $C_{2-6}$-alkenyl or aryl, or, (ii) $R^{9b}$ and $R^{9c}$ or $R^{9a}$ and $R^{9d}$ taken together form a —$(CH_2)_4$— bridge, or, (iii) $R^{9a}$ and $R^{9d}$ in formula IX both are halogen; or (iv) $R^{9a}$ and $R^{9d}$ in formula IX both are halogen and preferably chlorine.

$R^{a1}$, $R^{a2}$ and $R^{a3}$ are (i) independently $C_{1-6}$-alkyl, $C_{3-7}$-cycloalkyl, aryl, or heteroaryl, or, (ii) $R^{a1}$ and $R^{a2}$ or $R^{a2}$ and $R^{a3}$ or $R^{a1}$ and $R^{a3}$ form together a 1,5-bridged cyclooctyl group. Preferably $R^{a1}$, $R^{a2}$ and $R^{a3}$ are cyclohexyl or phenyl.

In another embodiment the ligand L in the ring-closing catalyst is VII, VIII or IX, $R^{10}$ and $R^{11}$ are $C_{1-6}$-alkyl or a phenyl group which is mono-, di- or tri-substituted with $C_{1-6}$-alkyl and (i) $R^{9a}$ and $R^{9c}$ are methyl or phenyl and $R^{9b}$ and $R^{9d}$ are hydrogen, or, (ii) $R^{9a}$ and $R^{9c}$ or $R^{9b}$ and $R^{9d}$ are taken together to form a —$(CH_2)_n$— bridge wherein n is 3 or 4. If chiral carbon atoms are present, both the racemic and the enantiomerically pure form are included within the scope of the invention.

In another embodiment the ligand L in the ring-closing catalyst is VII, VIII or IX, $R^{10}$ and $R^{11}$ are t-butyl, 1-adamantyl, isopropyl, 2-methylphenyl, 2,6-diisopropylphenyl or 2,4,6-trimethylphenyl, preferably 2,4,6-trimethylphenyl and (i) $R^{9a}$ and $R^{9c}$ are methyl or phenyl and $R^{9b}$ and $R^{9d}$ are hydrogen, or, (ii) $R^{9a}$ and $R^{9c}$ or $R^{9b}$ and $R^{9d}$ are taken together to form a —$(CH_2)_n$— bridge wherein n is 3 or 4 and $R^{9a-d}$ are hydrogen.

In another embodiment of the present invention the ligand L in the closing ruthenium catalyst is VIIa or VIIIa, $R^{10}$ and $R^{11}$ are t-butyl, 1-adamantyl, isopropyl, 2-methylphenyl, 2,6-diisopropylphenyl or 2,4,6-trimethylphenyl, most preferably 2,4,6-trimethylphenyl.

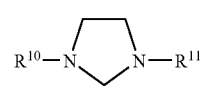

VIIa

IXa

In another embodiment of the present invention there is provided a process comprising steps (a) to (d) wherein the RCM catalyst for the ring closing of the diene in step (a) is selected from the group consisting of IIIa, IIIb, IIIc, IIId, IIIe, IIIf, IIIg and IIIh wherein $X^1$ and $X^2$ are preferably selected from a halogenide or a pseudo halogenide such as cyanide.

In another embodiment of the present invention there is provided a process comprising steps (a) to (d) wherein the RCM catalyst for the ring closing of the diene in step (a) is selected from the group consisting of IIIa, IIIb, IIIc, IIId, IIIe, IIIf, IIIg and IIIh wherein $X^1$ and $X^2$ are a halogenide.

In another embodiment of the present invention there is provided a process comprising steps (a) to (d) wherein the RCM catalyst for the ring closing of the diene in step (a) is selected from the group consisting of IIIa, IIIb, IIIc, IIId, IIIe, IIIf, IIIg and IIIh wherein $X^1$ and $X^2$ are chloro.

In another embodiment of the present invention there is provided a process comprising steps (a) to (d) wherein the RCM catalyst for the ring closing of the diene in step (a) is IIIc wherein Y is hydrogen.

In another embodiment of the present invention there is provided a process comprising steps (a) to (d) wherein the RCM catalyst for the ring closing of the diene in step (a) is selected from the group consisting of IIIa wherein $Y^1$ and $Y^2$ taken together with the carbon atom to which they are attached are VIa and G is hydrogen or phenyl.

In another embodiment of the present invention there is provided a process comprising steps (a) to (d) wherein the RCM catalyst for the ring closing of the diene in step (a) is IIIb; $Y^3$ is hydrogen and $R^b$ is $C_{1-6}$-alkyl $C_{2-6}$-alkenyl, halogen-$C_{1-6}$-alkyl, $C_{2-6}$-alkynyl, aryl, $C_{1-6}$-alkoxycarbonyl, $C_{1-6}$-alkylcarbonyl, mono-$C_{1-6}$-alkyl- or di-$C_{1-6}$-alkylamino, $C_{1-6}$-alkylaminocarbonyl, $C_{1-6}$-alkylthiocarbonyl, $C_{1-6}$-alkylsulfonyl, $C_{1-6}$-alkylsulfinyl or arylalkyl and a, b, c and d are independently hydrogen, $C_{1-6}$-alkyl, $C_{1-6}$ haloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$ haloalkyl sulfonyl amino, $SO_3$—$C_{1-6}$-alkyl, $OSi(C_{1-6}$-alkyl$)_3$ or $SO_2$—NR'R" wherein R' and R" are independently hydrogen, aryl or $C_{1-6}$-alkyl.

In another embodiment of the present invention there is provided a process comprising steps (a) to (d) wherein the RCM catalyst for the ring closing of the diene in step (a) is IIIb, $Y^3$ is hydrogen; $R^b$ is as outlined above, but preferably is $C_{1-6}$-alkyl or $C_{1-6}$ haloalkyl; a, b and d are hydrogen and c is hydrogen, halogen, nitro, $C_{1-6}$-alkylcarbonyl amino, aryl carbonyl amino, aryl sulfonyl amino, alkyl sulfonyl amino, $C_{1-6}$ haloalkyl sulfonyl amino or $SO_2$—NR'R" wherein (i) R' and R" independently are hydrogen, $C_{1-6}$-alkyl or aryl or (ii) R' and R" together with the N atom to which they are attached form a carbocycle.

In another embodiment of the present invention there is provided a process comprising steps (a) to (d) wherein the RCM catalyst for the ring closing of the diene in step (a) is IIIb and $Y^3$ is hydrogen; $R^b$ is as outlined above, but preferably stands for $C_{1-6}$-alkyl and $C_{1-6}$ haloalkyl; a, b and d are hydrogen and c is hydrogen, Cl, nitro, $SO_2$—NR'R" wherein (i) R' and R" independently are hydrogen, $C_{1-6}$-alkyl or aryl, or (ii) R' and R" together with the N atom to which they are attached form a carbocycle.

In another embodiment of the present invention there is provided a process comprising steps (a) to (d) wherein the RCM catalyst for the ring closing of the diene in step (a) is selected from the group consisting of IIId, IIIf, IIIg and IIIh wherein $Y^4$ and $Y^5$ are independently hydrogen, $C_{1-6}$-alkyl, aryl or arylthio.

In another embodiment of the present invention there is provided a process comprising steps (a) to (d) wherein the RCM catalyst for the ring closing of the diene in step (a) is IIId; $Y^4$ is hydrogen, $C_{1-6}$-alkyl, aryl or arylthio and a, b, c and d are independently hydrogen, $C_{1-6}$-alkyl, $C_{1-6}$ haloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alklylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$ haloalkyl sulfonyl amino, $SO_3$—$C_{1-6}$-alkyl, $OSi(C_{1-6}$-alkyl$)_3$ or $SO_2$—NR'R" wherein R' and R" are independently hydrogen, aryl or $C_{1-6}$-allyl.

$R^{1a}$ is hydrogen, hydroxy, $C_{1-6}$-alkyl, $C_{1-6}$-alkoxy, $C_{2-6}$-alkenyloxy, $C_{3-8}$-cycloalkyloxy, halogen-$C_{1-6}$-alkyloxy, aryl, aryloxy, $C_{1-6}$-alkylthio, arylthio, or —NR'R" wherein (i) R' and R" independently are hydrogen, $C_{1-6}$-alkyl, $C_{3-8}$-cycloalkyl, aryl or aryl-$C_{1-6}$-alkyl or (ii) R' and R" together with the nitrogen atom to which they are attached form a 5 to 8 member carbocycle which may contain nitrogen, oxygen or sulfur as additional hetero atom.

$R^{2a}$ and $R^{3a}$ are independently hydrogen, $C_{1-6}$-alkyl, $C_{3-8}$-cycloalkyl, aryl or $C_{7-18}$-arylalkyl.

In another embodiment of the present invention there is provided a process comprising steps (a) to (d) wherein the RCM catalyst for the ring closing of the diene in step (a) is IIId and $Y^4$ is hydrogen; $R^b$ is as outlined above, but preferably is $C_{1-6}$-alkyl and $C_{1-6}$ haloalkyl; a, b and d are hydrogen and c is hydrogen, halogen, nitro, $C_{1-6}$-alkylcarbonyl amino, aryl carbonyl amino, aryl sulfonyl amino, alkyl sulfonyl amino, $C_{1-6}$ haloalkyl sulfonyl amino or $SO_2$—NR'R" wherein (i) R' and R" are independently hydrogen, $C_{1-6}$-alkyl or aryl or (ii) R' and R" together with the nitrogen atom to which they are attached form a carbocycle.

$R^{1a}$ is hydroxy, $C_{1-6}$-alkyl, $C_{1-6}$-alkoxy, or —NR'R" wherein (i) R' and R" are independently of each hydrogen, $C_{1-6}$-alkyl, $C_{3-8}$-cycloalkyl, aryl or aryl-$C_{1-6}$-alkyl or (ii) R' and R" together with the nitrogen atom to which they are attached form a 5 to 8 member carbocycle which may contain nitrogen, oxygen or sulfur as additional hetero atom.

$R^{2a}$ and $R^{3a}$ are independently hydrogen or $C_{1-6}$-alkyl.

In another embodiment of the present invention there is provided a process comprising steps (a) to (d) wherein the RCM catalyst for the ring closing of the diene in step (a) is IIIb, $Y^3$ is hydrogen, $R^b$ is $C_{1-6}$-alkyl or $C_{1-6}$ haloalkyl; a, b and d are hydrogen and c is hydrogen, Cl, nitro, $SO_2$—NR'R" wherein (i) R' and R" are independently hydrogen, $C_{1-6}$-alkyl or aryl or (ii) R' and R" together with the nitrogen atom to which they are attached form a carbocycle.

$R^{1a}$ is hydroxy, $C_{1-6}$-alkyl, $C_{1-6}$-alkoxy, or —NR'R" wherein (i) R' and R" are independently hydrogen, $C_{1-6}$-alkyl, $C_{3-8}$-cycloalkyl, aryl or aryl-$C_{1-6}$-alkyl or (ii) R' and R" together with the nitrogen atom to which they are attached form a 5 to 8 member carbocycle which may contain nitrogen, oxygen or sulfur as additional hetero atom;

$R^{2a}$ and $R^{3a}$ are independently H or $C_{1-6}$-alkyl.

In another embodiment of the present invention there is provided a process comprising steps (a) to (d) wherein the RCM catalyst for the ring closing of the diene in step (a) is IIIe wherein Arene is benzene, p-cymene, mesitylene or, p-xylene.

In another embodiment of the present invention there is provided a process comprising steps (a) to (d) wherein the RCM catalyst for the ring closing of the diene in step (a) is selected from the ruthenium complexes in TABLE I.

TABLE I

| Catalyst Number | Catalyst Structure | Chemical Short Name |
|---|---|---|
| 5000 | 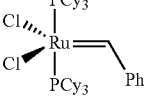 | [RuCl$_2$(PCy$_3$)$_2$(benzylidene)]<br>CAS No. 172222-30-9; a) |
| 5001 | 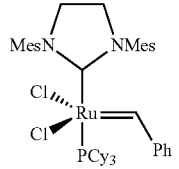 | [RuCl$_2$(PCy$_3$)(ImH$_2$Mes)(benzylidene)]<br>CAS No. 246047-72-3; a) |
| 5002 | 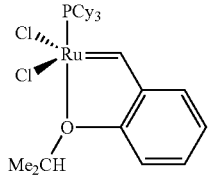 | [RuCl$_2$(=CH(2-iPrOPh))(PCy$_3$)]<br>CAS No. 203714-71-0; a) |
| 5003 | 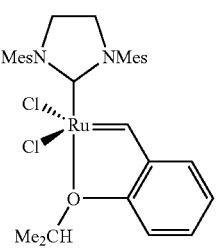 | [RuCl$_2$(=CH(2-iPrOPh))(ImH$_2$Mes)]<br>CAS No. 301224-40-8; a) |
| 5006 | 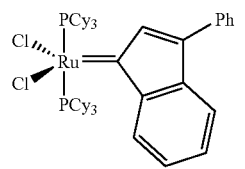 | [RuCl$_2$(PCy$_3$)$_2$(3-phenylindenyl-1-idene)]<br>CAS No. 250220-36-1; c) |
| 5008 | 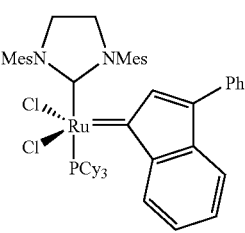 | [RuCl$_2$(PCy$_3$)(ImH$_2$Mes)(3-phenylindenyl-1-idene)]<br>CAS No. 536724-67-1; c) |
| 5016 | 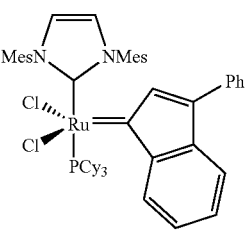 | [RuCl$_2$(3-phenylindenyl-1-idene)(ImMes)(PCy$_3$)]<br>CAS No. 254972-49-1; d) |

TABLE I-continued

| Catalyst Number | Catalyst Structure | Chemical Short Name |
| --- | --- | --- |
| 5017 | | [RuCl$_2$(3-phenylindenyl-1-idene)(ImMes)(PPh$_3$)]<br>CAS No. 254972-47-9; d) |
| 5024 | | [RuCl$_2$(=CH(2-iPrO, 5-ClPh))(ImH$_2$Mes)]<br>CAS No. 918870-68-5; b) |
| 5025 | | [RuCl$_2$(=CH(7-CF$_3$, 5-Cl-8-quinoline))-(ImH$_2$Mes)]; e) |
| 5040 | | [RuCl$_2$(=CHSPh)(ImH$_2$Mes)(PCy$_3$)]; g) |
| 5041 | | [RuCl$_2$(3-phenylindenyl-1-idene)-(isobutylphobane)$_2$]<br>CAS No. 894423-99-5; c) |
| 5047 | | [RuCl$_2$(=CHPh)(ImH$_2$Mes)(m-Br-Pyr)$_2$]<br>CAS No. 477218-66-9; a) |

TABLE I-continued

| Catalyst Number | Catalyst Structure | Chemical Short Name |
|---|---|---|
| 5055 | | [RuCl$_2$(=CH((o-OCH(CH$_3$)(C=O)CH$_3$)Ph)(ImH$_2$Mes) Prepared according to WO 2008/034552 A1 |
| 5056 | | [RuCl$_2$(=CH(o-OCH(Me)CO$_2$Me)Ph)(ImH$_2$Mes)] CAS No. 837392-94-6 M. Bieniek, R. Bujok, M. Cabaj, N. Lugan, G. Lavigne, D. Arlt, K. Grela, *J. Am. Chem. Soc.* 2006, 128, 13652. |
| 5057 | | [RuCl$_2$(=CH(o-OCH(Me)CO$_2$H)-Ph)(ImH$_2$Mes)] CAS No. 959710-27-1 Generated in situ according to: R. Gawin, A. Makal, K. Wozniak, M. Mauduit, K. Grela, *Angew. Chem.Int. Ed.* 2007, 46, 7206. |
| 5058 | | [RuCl$_2$(=CH(o-OCH(Me)CONEt$_2$)Ph)-(ImH$_2$Mes)] f) |
| 5059 | | [RuCl$_2$(=CH(o-OCH(Me)CONH$_2$)-Ph)(ImH$_2$Mes)] f) |
| 5062 | | [RuCl$_2$(ImMes)(p-cymene)] CAS NO 244187-82-4 L. Jafarpour, J. Huang, E. D. Stevens, S. Nolan, *Organometallics* 1999, 18, 3760. |

TABLE I-continued

| Catalyst Number | Catalyst Structure | Chemical Short Name |
|---|---|---|
| 5064 | | [RuCl$_2$(=CH(o-OCH(Me)CO—N-Morpholine)Ph)(ImH$_2$Mes)] f) |
| 5065 | | [RuCl$_2$(=CH(o-OCH(Me)CO—N-Pyrrolidine)Ph)(ImH$_2$Mes)] f) |
| 5072 | | [RuCl$_2$(=CH(o-OCMe$_2$CO—N-Pyrrolidine)Ph)(ImH$_2$Mes)] f) |
| 5073 | | RuCl$_2$(=CH(o-OCH$_2$CO—N-Pyrrolidine)Ph)(ImH$_2$Mes)] f) | a) Commercially available from Sigma-Aldrich Chemie GmbH, Postfach, CH-9471 Buchs, Switzerland:
b) Commercially available from Zannan Pharma Ltd. 4299 Jindu Road, Bld. 3, Shanghai, 201108, P.R. China and Strem Chemicals Inc., 7 Mulliken Way, Newburyport, MA 01950-4098, USA.
c) Commercially available from Umicore & Co., Rodenbacher Chaussee 4, D-63403 Hanau, Germany and Strem Chemicals Inc., 7 Mulliken Way, Newburyport, MA 01950-4098, USA.
d) Commercially available from Degussa AG, Rodenbacher Chaussee 4, D-63403 Hanau, Germany.
e) Prepared according to WO2008/000644 A1.
f) Prepared according to EP Appl. No. 08154367.0, filed Apr. 11, 2008.
g) Commercially available from Strem Chemicals, Inc., Postfach 1215, KEHL, 77672, Germany.

In another embodiment of the present invention there is provided a process comprising steps (a) to (d) wherein the RCM catalyst for the ring closing of the diene in step (a) is selected from the following complexes:

[RuCl$_2$(PCy$_3$)(ImH$_2$Mes)(benzylidene)],

[RuCl$_2$(=CH(2-iPrOPh))(ImH$_2$Mes)],

[RuCl$_2$(PCy$_3$)(ImH$_2$Mes)(3-phenylindenyl-1-idene)],

[RuCl$_2$(3-phenylindenyl-1-idene)(ImMes)(PCy$_3$)],

[RuCl$_2$(=CH(o-OCH(Me)CO$_2$Me)Ph)(ImH$_2$Mes)],

[RuCl$_2$(=CH(o-OCH(Me)CONEt$_2$)Ph)(ImH$_2$Mes)],

[RuCl$_2$(=CH(o-OCH(Me)CO—N-Morpholine)Ph)(ImH$_2$Mes)],

[RuCl$_2$(=CH(o-OCH(Me)CO—
N-Pyrrolidine)Ph)(ImH$_2$Mes)],

[RuCl$_2$(=CH(o-OCMe$_2$CO—
N-Pyrrolidine)Ph)(ImH$_2$Mes)] and

[RuCl$_2$(=CH(o-OCH$_2$CO—
N-Pyrrolidine)Ph)(ImH$_2$Mes)].

The RCM reaction is usually performed in an organic solvent, preferably in an aromatic organic solvent such as in benzene, toluene or mesitylene or in halogenated aromatic solvents such as in polyfluorinated benzenes like α,α,α-trifluorotoluene, octafluorotoluene, 1,2-difluorobenzene or hexafluorobenzene. Also halogenated hydrocarbons such as dichloromethane or dichloroethane are suitable solvents. The solvents may be used as single solvent or as a mixture of different solvents. In addition an aliphatic hydrocarbon co-solvent such as pentane, hexane or heptane may be used.

The reaction temperature may range from 20° C. to 140° C., preferably 40° C. to 100° C. and even more preferred 50° C. to 90° C. The molar substrate to catalyst ratio S/C is usually selected in a range of 20 to 10000, but preferably in a range of 150 to 4000.

The exact substrate concentration is not critical; it is typically between 0.1 and 25%. From a technical standpoint it is preferable to use a substrate concentration between 5 and 15%. Typically an inert gas is bubbled through the reaction mixture or under a slight vacuum is applied.

The macrocyclic ester of formula I can be isolated by applying methods known to the skilled in the art such as by column chromatography or by crystallization. The metathesis reaction mixture can also, after a simple extractive work-up, be used directly in the next step.

To remove most catalyst from the solution of the macrocyclic ester I, the reaction mixture can be treated with a complexing agent such as ethylenediaamine and the resulting soluble ruthenium species is extracted into aqueous acid. The amount of ethylenediamine is not critical; it can be used in a 1:1 to 100:1 molar ratio relative to the catalyst, preferentially in 20:1 to 70:1 molar ratio.

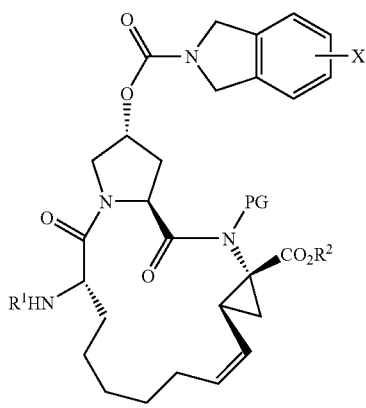
(I)

The macrocyclic esters of the formula I wherein $R^1$ and PG are amino protecting groups, $R^2$ is $C_{1-4}$-alkyl and X is halogen are compounds not known in the art and thus represent a further embodiment of the present invention.

In another embodiment the macrocyclic ester of formula I $R^1$ is Boc, $R^2$ is ethyl, PG is $C_{1-6}$-alkylcarbonyl, arylcarbonyl or $C_{1-6}$-alkoxycarbonyl and the moiety XXIVa is XXIVb. In yet another embodiment the macrocyclic ester of formula I and PG is benzoyl.

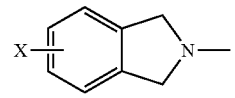
XXIVa

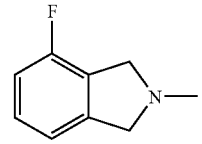
XXIVb

Step (b) requires the hydrolysis of the ester and the removal of the protection group PG from the macrocyclic ester of formula I and the formation of the macrocyclic acid of formula XX. In a preferred embodiment the macrocyclic ester is a compound of formula I wherein $R^1$ is Boc, $R^2$ is ethyl, PG is $C_{1-6}$-alkylcarbonyl, arylcarbonyl or $C_{1-6}$-alkoxycarbonyl and the moiety XXIVa is XXIVb. In yet another embodiment the PG is benzoyl.

The hydrolysis and the removal of the protection group PG can usually be accomplished by treatment with an aqueous alkali hydroxide solution such as with an aqueous sodium hydroxide solution in solvents like tetrahydrofuran, methanol or ethanol or mixtures thereof at a temperature of 0° C. to 40° C.

In the case of PG is $C_{1-6}$-alkoxycarbonyl its removal of the carbamate can usually be accomplished by treatment with an acid, such as with hydrochloric acid, sulfuric acid, trifluoroacetic acid, methanesulfonic acid, p-toluenesulfonic acid, benzenesulfonic acid. As the acid treatment may remove the Boc-group $R^1$ requiring subsequent reintroduction of the Boc group.

After neutralization of the reaction mixture, usually with hydrochloric acid, the macrocyclic acid of formula XX can be isolated by way of extraction with a suitable solvent such as with dichloromethane. Crystallization in a suitable solvent, preferably in tetrahydrofuran leads to a crystalline product with a purity of over 98% (HPLC, area).

In a further embodiment of the invention the macrocyclic acid of formula XX can be obtained directly without isolation of the intermediate products from the intermediate of formula XIVa wherein $R^1$, $R^2$ and X have the meaning as described above.

SCHEME 3

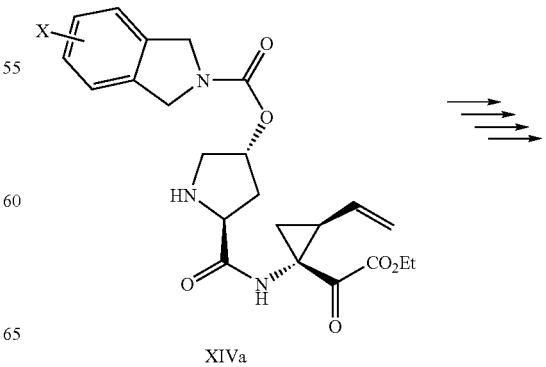
XIVa

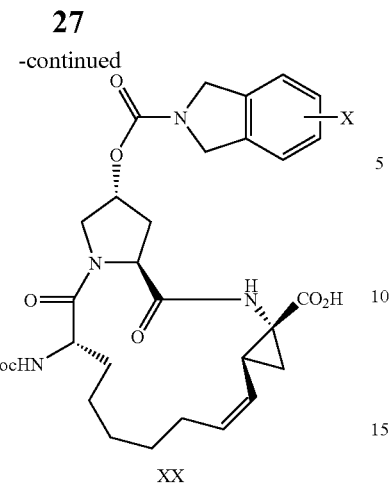

XX

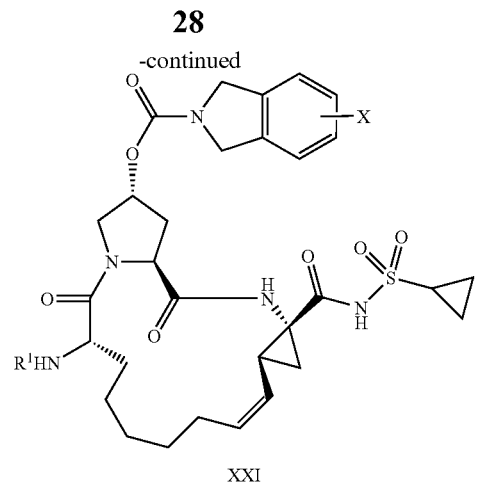

XXI

Step (c) is the coupling of the macrocyclic acid of formula XX wherein $R^1$ is an amino protecting group and X is halogen with cyclopropyl sulfonamide to form the macrocyclic sulfonamide of formula XXI. In a first step the macrocyclic acid of formula XX is reacted with acetic acid anhydride in the presence of an inorganic base, such as with an alkali carbonate like sodium carbonate, and a suitable organic solvent such as with tetrahydrofuran to afford an azlactone intermediate of the formula XXIII which is condensed with cyclopropyl sulfonamide

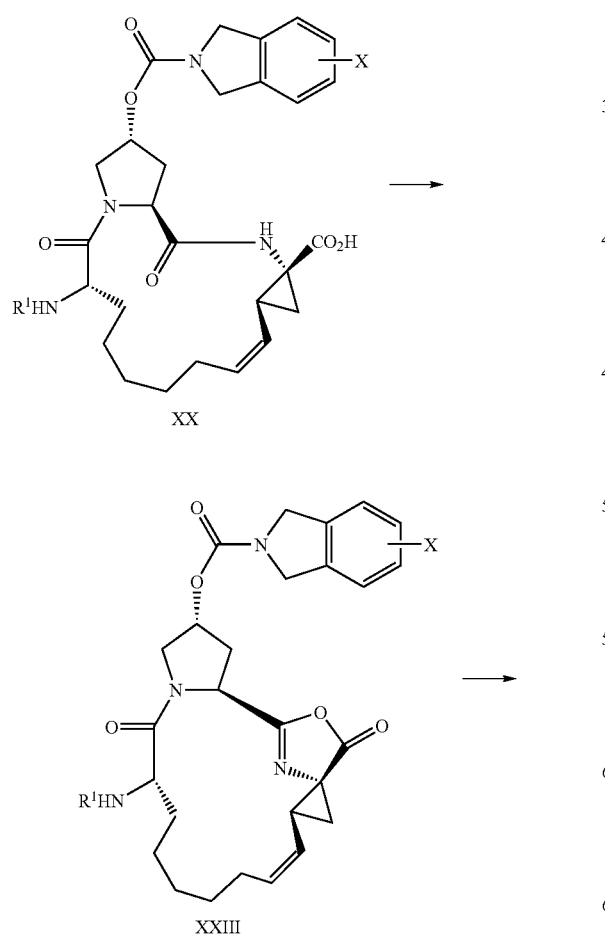

In a one embodiment the macrocyclic acid of the formula XXb is used

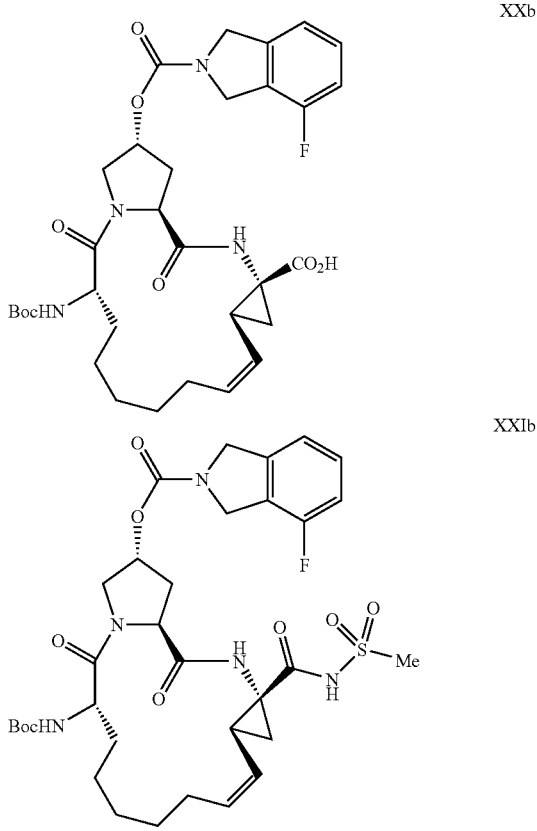

Formation of the azlactone intermediate is expediently performed at a temperature of 10° C. to 50° C. The azlactone intermediate typically is not be isolated but further reacted in situ with cyclopropyl sulfonamide in the presence of an inorganic base, such as with an alkali carbonate like potassium carbonate to afford the macrocyclic sulfonamide of formula XXI. The condensation of the azlactone with cyclopropyl sulfonamide is expediently performed at a temperature of 50° C. to 70° C.

Upon completion of the reaction the reaction mixture can be treated with water. After separation and removal of the water phase the organic phase may further be diluted with a suitable organic solvent such as with ethyl acetate or toluene and washed e.g. with an aqueous sulfuric acid and water. Isolation of the macrocyclic sulfonamide of formula XXI can then be accomplished by a solvent switch to ethanol followed by addition of the ethanolic solution to water thereby causing precipitation of the desired product.

In a one embodiment of the present invention the macrocyclic sulfonamide of formula XXI is not be isolated. The organic phase which has been treated as hereinbefore described is dried by continuous azeotropic distillation. The resulting solution of XXI can then be used directly in subsequent step (d).

Step (d) requires the treatment of the macrocyclic sulfonamide of formula XXI with a sodium base to form the end product, i.e. the macrocyclic compound of formula XXII. In a one embodiment the macrocyclic sulfonamide XXIb is used.

The water free mixture obtained from step (c) is treated with a sodium base to afford the sodium salt. Typically sodium hydroxide, preferably in aqueous solution, or sodium methylate or sodium ethoxide, preferably in alcoholic solution, are used. In one embodiment of the present invention, XXI is treated methanolic sodium methoxide at a temperature of 0° C. and 50° C.

The reaction mixture can be treated with a mixture of a suitable organic solvent such as ethyl acetate and water where after the crystals of the sodium compound of formula XXII, preferably the compound of formula XXIIb can be collected in good purity and yield.

EXAMPLES

Abbreviations

Boc=tert-butyloxy-carbonyl
r.t.=room temperature
ImH$_2$Mes=1,3-bis-(2,4,6-trimethylphenyl)-2-imidazolidinylidene
ImMes=1,3-bis-(2,4,6-trimethylphenyl)-2-imidazolylidene
ImH$_2$Pr=1,3-bis-(2,6-diisopropylphenyl)-2-imidazolidinylidene
RCM=ring closing metathesis
S/C=molar substrate-to-catalyst ratio
Mes=2,4,6-Trimethylphenyl
a %=HPLC area %
Diene XV: 4-Fluoro-1,3-dihydro-isoindole-2-carboxylic acid, (3R,5S)-1-[(S)-2-tert-butoxycarbonylamino-non-8-enoyl]-5-[(1R,2S)-1-ethoxycarbonyl-2-vinyl-cyclopropyl-carbamoyl]-pyrrolidin-3-yl ester.

XV

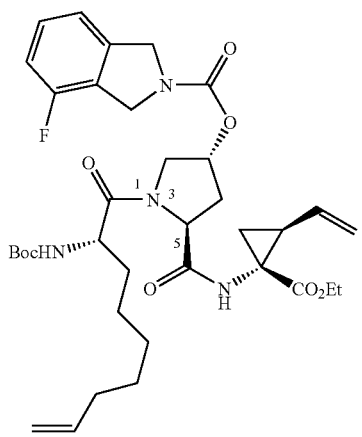

N-acetyl-Diene IIb: 4-Fluoro-1,3-dihydro-isoindole-2-carboxylic acid (3R,5S)-5-[acetyl-((1R,2S)-1-ethoxycarbonyl-2-vinyl-cyclopropyl)-carbamoyl]-1-((S)-2-tert-butoxycarbonylamino-non-8-enoyl]-pyrrolidin-3-yl ester N-propionyl-Diene IIc: 4-Fluoro-1,3-dihydro-isoindole-2-carboxylic acid (3R,5S)-1-((S)-2-tert-butoxycarbonylamino-non-8-enoyl)-5-[(((1R,2S)-1-ethoxycarbonyl-2-vinyl-cyclopropyl)-propionyl-carbamoyl]-pyrrolidin-3-yl ester N-BOC-Diene IIa: 4-Fluoro-1,3-dihydro-isoindole-2-carboxylic acid (3R,5S)-1-((S)-2-tert-butoxycarbonylamino-non-8-enoyl)-5-[tert-butoxycarbonyl-((1R,2S)-1-ethoxycarbonyl-2-vinyl-cyclopropyl)-aminocarbonyl]-pyrrolidin-3-yl ester N-Benzoyl-Diene IId: 4-Fluoro-1,3-dihydro-isoindole-2-carboxylic acid (3R,5S)-5-[benzoyl-((1R,2S)-1-ethoxycarbonyl-2-vinyl-cyclopropyl)-carbamoyl]-1-((S)-2-tert-butoxycarbonylamino-non-8-enoyl)-pyrrolidin-3-yl ester N-Acetyl-RCM-Ester Ib: (Z)-(1S,4R,6S,14S,18R)-3-Acetyl-14-tert-butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-4-carboxylic acid ethyl ester.

The atom numbering is shown below:

Ib

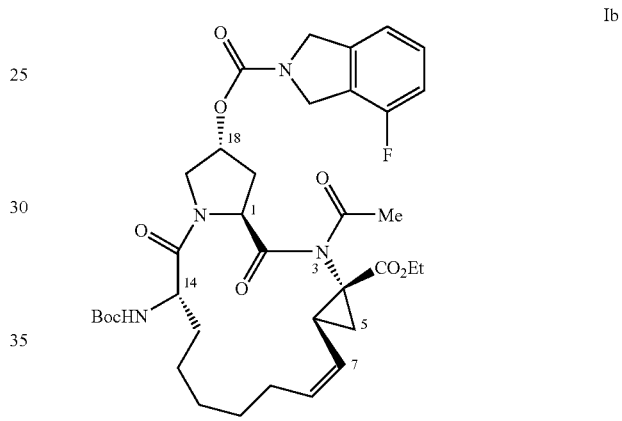

N-Propionyl-RCM-Ester Ic:

(Z)-(1S,4R,6S,14S,18R)-14-tert-Butoxycarbonylamino-18-(4-fluoro-1,3-dihydro-isoindole-2-carbonyloxy)-2,15-dioxo-3-propionyl-3,16-diaza-tricyclo[14.3.0.0$^{4,6}$]nonadec-7-ene-4-carboxylic acid ethyl ester.

N-BOC-RCM-Ester-Ia:

(Z)-(1S,4R,6S,14S,18R)-14-tert-Butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-3,4-dicarboxylic acid 3-tert-butyl ester 4-ethyl ester.

N-Benzoyl-RCM-Ester Id:

(Z)-(1S,4R,6S,14S,18R)-3-Benzoyl-14-tert-butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-4-carboxylic acid ethyl ester.

RCM-Carboxylic Acid XXb:

(Z)-(1S,4R,6S,14S,18R)-14-tert-Butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-4-carboxylic acid.

(Z)-(1S,4R,6S,14S,18R)-14-tert-Butoxycarbonylamino-18-(4-fluoro-1,3-dihydro-isoindole-2-carbonyloxy)-2,15-dioxo-3,16-diaza-tricyclo[14.3.0.0$^{4,6}$]nonadec-7-ene-4-carboxylic acid ethyl ester.

The catalysts tested are tabulated in TABLE I.

Preparation of diene compounds IIa to IId:

Example A

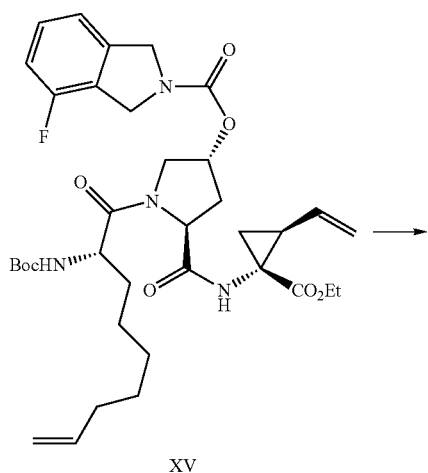

To a solution of the diene XV (40.0 g, 53.80 mmol, 92.1% content) in 330 mL of tetrahydrofuran were added under argon 22.70 mL (163.5 mmol) of triethylamine, 6.90 g (161.6 mmol) of lithium chloride and 15.0 mL (159 mmol) of acetic anhydride and the mixture was stirred at 60° C. (internal temperature) during 6 h, after which time only 2 area % of diene XV had remained unreacted. The slightly cloudy reaction mixture was cooled, filtered and the precipitate washed with tetrahydrofuran. The combined filtrates were rotary evaporated to dryness (40° C./180 mbar). The oily residue was dissolved in 500 mL of ethyl acetate and extracted with 300 mL of hydrochloric acid 0.5 M. The aqueous phase was back-extracted with a total of 1 L ethyl acetate. The combined organic phases were washed with 300 mL of hydrochloric acid, 300 mL of deionized water, then dried with 70 g of sodium sulfate and filtered. The filtrate was treated with decolorizing charcoal, filtered and rotary evaporated. The oily residue was purified by column chromatography (1 kg silica gel 0.040-0.063 mm) and eluted with a mixture of heptane and ethyl acetate using a gradient from 9:1 to 3:2. Collection of the fractions containing the desired product in comparable purity and evaporation to dryness to constant weight (40° C./16 mbar/3 h) afforded 27.6 g of diene-acetate IIb as a white solid with 96 area % according to HPLC and 85% according to NMR.

HPLC method: same as Example 1. Retention times: diene XV 8.66 min, diene-acetate IIb 10.1 min.

MS [MH]$^+$ 657.4 u, 727.4 [MNH4]$^+$; NMR (selected peaks, δ, CDCl$_3$): (CH$_3$C=O) 2.26 (s, 3H), (CH$_3$—CH$_2$) 1.22 (t, 3H), (CH$_3$—$\overline{CH_2}$) 4.13 (m, 2H), (t-Bu) $\overline{1.33}$ (s, 9H); IR: Carbonyl signals $\overline{at\,1710}$ cm$^{-1}$ (strong, broad), 1632 cm$^{-1}$ (medium, broad).

Example B

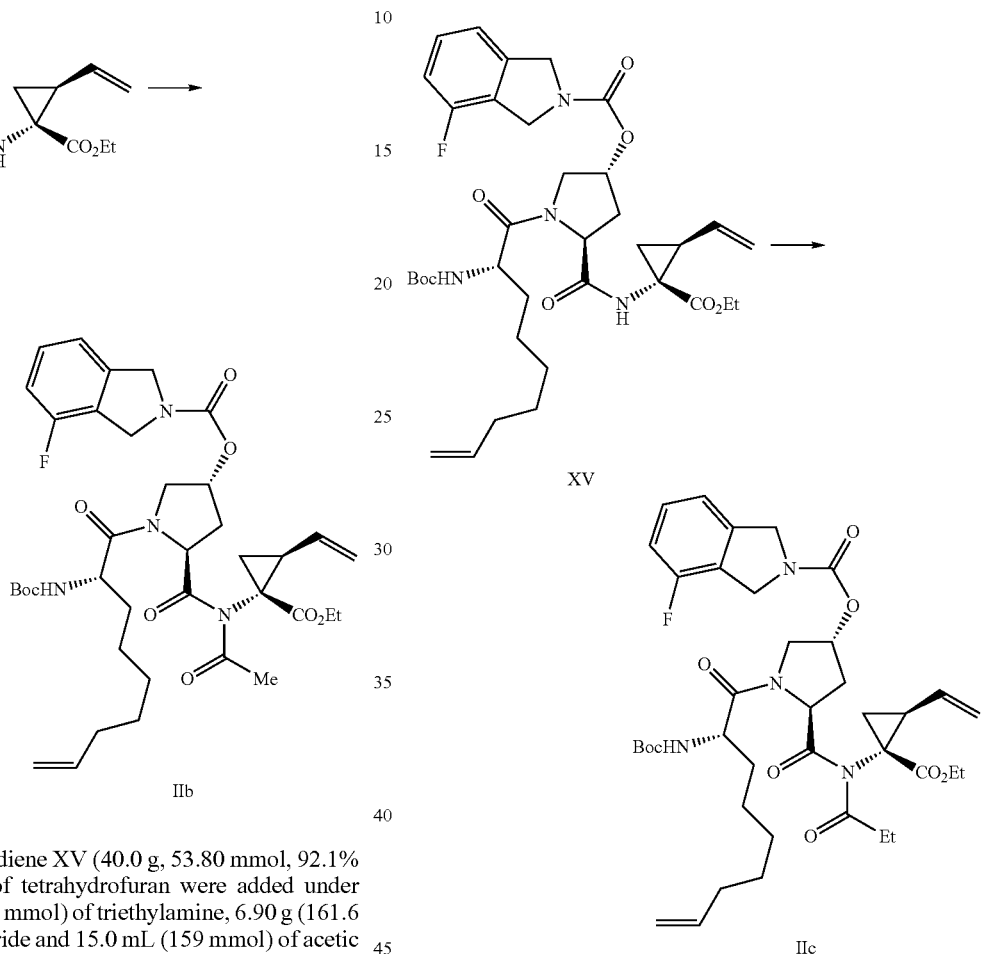

To a solution of the diene XV (15.3 g, 22 mmol) in 120 mL of tetrahydrofuran were added under argon 6.8 g (67 mmol) of triethylamine, 2.9 g (67 mmol) lithium chloride and 6.4 g (49 mmol) of propionic acid anhydride. The mixture was heated to 80° C. for 10 h 30 min and then cooled to room temperature at which it was stirred for another 11 h. After this time in-process control showed 99.6% (HPLC) conversion. o the mixture 100 mL water and 3.5 mL aqueous HCl (37%) were added. The biphasic mixture was extracted with ethyl acetate, the aqueous layer was separated off and the organic layer was washed with 100 mL of brine. The aqueous layers were back extracted with 200 mL of ethyl acetate. The combined organic layers were dried over sodium sulfate, filtered and concentrated to dryness. 26.8 g of an oily brown residue was obtained. The oily residue was purified by column chromatography (600 g silica gel 0.040-0.063 mm) and eluted with a mixture of hexane and ethyl acetate using a gradient from 7:3 to 7:4. Collection of the fractions containing the desired product in comparable purity and evaporation to dryness afforded 16.8 g of IIc as a colorless solid with a purity of 97.6 area % according to HPLC.

HRMS, [MH]$^+$785.41315; NMR (δ, DMSO-D6, 150° C.): 1.09 (t, 3H), 1.15 (t, 3H), 1.30 (s, 9H), 1.3-1.4 (m, 6H), 1.52 (m, 1H), 1.60-1.69 (m, 1H), 1.74-1.82 (m, 1H), 1.92-1.95 (m, 1H), 1.99-2.04 (m, 2H), 2.21-2.27 (m, 1H), 2.41 (m, 1H), 2.48-2.56 (m, 1H), 2.61-2.71 (m, 1H), 3.81 (m, 1H), 3.89 (d, br, 1H), 4.09 (q, 2H), 4.17 (q, br, 1H), 4.66 (s, 4H), 4.90 (m, 1H), 4.96 (m, 1H), 5.14 (m, 1H), 5.16-5.33 (m, 3H), 5.74-5.85 (m, 2H), 6.0 (s, br, 1H), 7.01 (dd, 1H), 7.11 (d, 1H), 7.30 (m, 1H); IR (selected absorptions, cm$^{-1}$): 3294, 2980, 2934, 1705, 1631, 1596, 1518, 996, 911, 776.

Example C in comparable purity and evaporation to dryness afforded 17.3 g of N-BOC-diene IIa as a yellowish solid with 98.5 area % according to HPLC.

HRMS, [MH]$^+$785.41315; NMR (δ, DMSO-D6, 120° C.): 1.15 (t, 3H), 1.28 (s, 9H), 1.25-1.40 (m, 6H), 1.47 (s, 9H), 1.52 (m, 1H), 1.62 (m, 1H), 1.79 (m, 1H), 2.01 (m, 2H), 2.23 (m, 1H), 2.29 (m, 1H), 1.48-2.55 (m, 2H), 3.82 (m, 1H), 4.0 (m, 1H), 4.06 (m, 2H), 4.14 (m, 1H), 4.66 (s, 4H), 4.90 (m, 1H), 5.30 (m, 6H), 5.78 (m, 2H), 6.25 (s, br, 1H), 7.03 (m, 1H), 7.12 (d, 1H), 7.31 (m, 1H); IR (selected absorptions, cm$^-$): 3289, 1719, 1634, 1523, 1019, 997, 776.

Example D

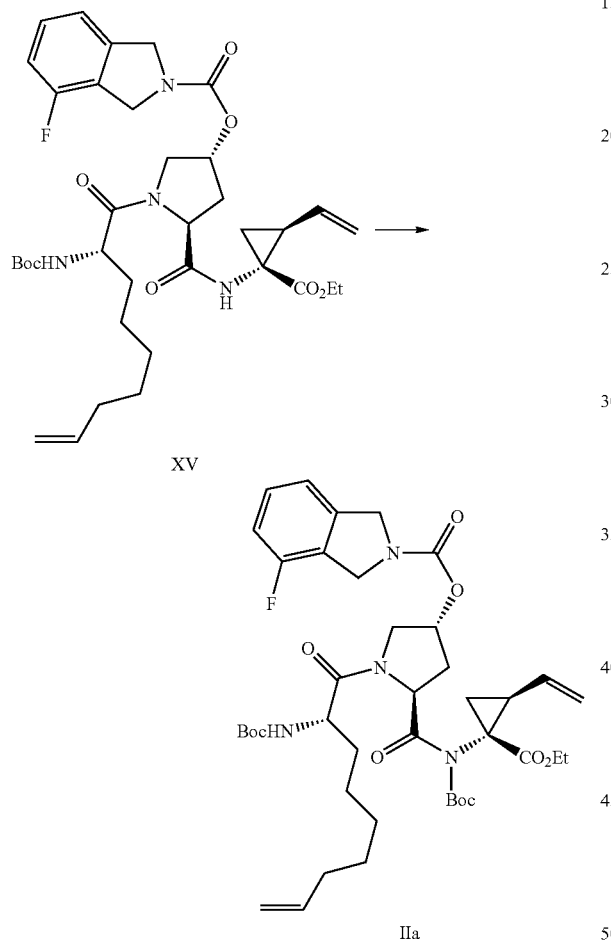

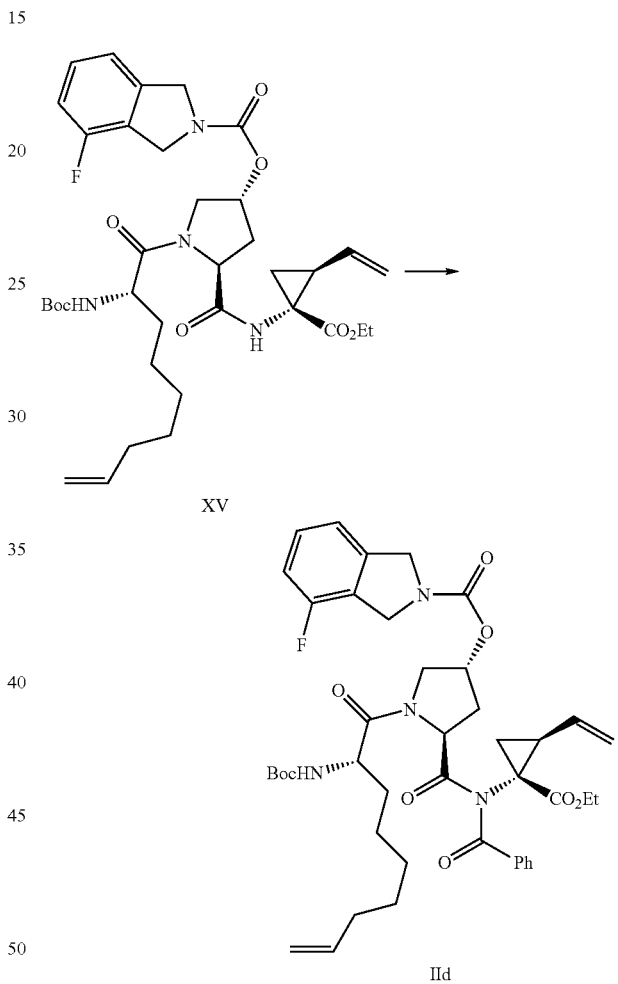

To a solution of the diene XV (15.3 g, 22 mmol) in 90 mL of ethyl acetate were added under argon 0.82 g (6.7 mmol) of 4-dimethylamino pyridine. The mixture was cooled to 0° C. and 6.9 g (31 mmol) of di-tert-butyl dicarbonate were added within 5 minutes. The reaction mixture was heated to 23° C. an stirred at this temperature for 225 minutes. After this time only 3.8 area % of diene XV had remained unreacted. To the mixture 50 mL of 0.1N aqueous HCl were and 50 mL of ethyl acetate were added. The aqueous phase was separated and extracted with 100 mL of ethyl acetate. The organic layer was washed with 50 mL of water, dried over sodium sulfate, filtered and concentrated. 21.1 g of a brown oily residue was obtained. The oily residue was purified by column chromatography (silica gel 0.040-0.063 mm) and eluted with a mixture of hexane and ethyl acetate using a gradient from 8:2 to 7:3. Collection of the fractions containing the desired product To a solution of the diene XV (30.0 g, 41.67 mmol) in 200 mL of toluene were added under argon in an ice bath 7.20 mL (79.2 mmol) of benzoyl chloride. Then a 2 M solution of lithium tert-butoxyde in tetrahydrofuran (38.5 mL, 77.0 mmol) was added within 5 minutes and the reaction mixture was stirred at the same temperature for 30 minutes. After this time only 4.6 area % of diene XV had remained unreacted. After dropwise addition of a 2 M sodium hydroxide solution (50 mL, 100 mmol) the organic phase was separated, extracted with 50 mL each of water, 1 M hydrochloric acid and water, dried with sodium sulphate and evaporated to dryness. The resulting brown oily residue was purified by column chromatography (silica gel 0.040-0.063 mm) and eluted with a mixture of heptane and ethyl acetate using a gradient from 3:1 to 1:1. Collection of the fractions containing the desired product in comparable purity and evaporation to dryness afforded 26.8 g (78.2%) of N-benzoyl-diene IId as a yellowish solid with 96.0 area % according to HPLC.

HRMS: [MH]$^+$789.3858; IR (nujol, cm$^{-1}$, selected signals): 1708, 1640 (C=O)

RCM Examples

Comparative Example A

RCM with no N-Substitution

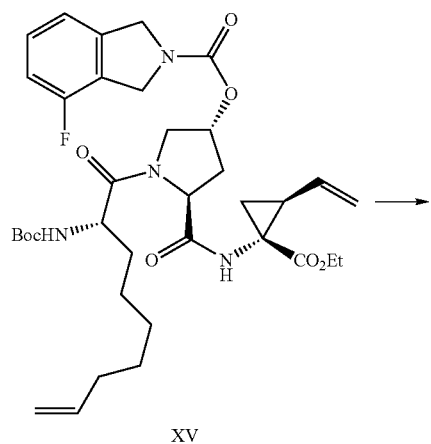

XV

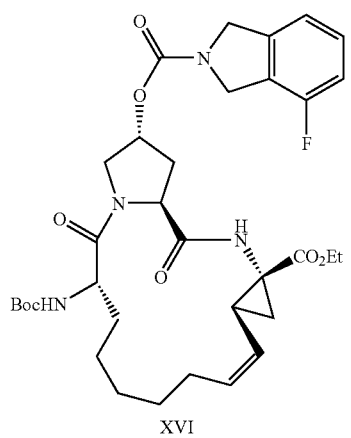

XVI

To a solution of 6.60 g (5.00 mmol) of diene XV (as a 51.4% solution in toluene) in 390 mL of toluene was added at 70° C. under vacuum (pressure=ca. 0.26 bar) by dropping funnel a solution of 3.59 mg (0.005 mmol) of catalyst 5058 in 20 mL of toluene. The catalyst was added during ca. 1 h. Under these conditions a small amount of toluene (19 mL) distilled off in the course of the reaction. After 2 h of total reaction time 17 µl (0.252 mmol) of ethylene diamine were added at ambient pressure, the reaction mixture was concentrated under vacuum, washed with 0.5 M aqueous solution of hydrochloric acid, treated with decolorizing charcoal and evaporated to dryness. RCM-ester XVI was isolated as an off-white solid (3.58 g) with 84.2 a % purity (75.7% content, 82.5% yield).

Example 1

S/C 20

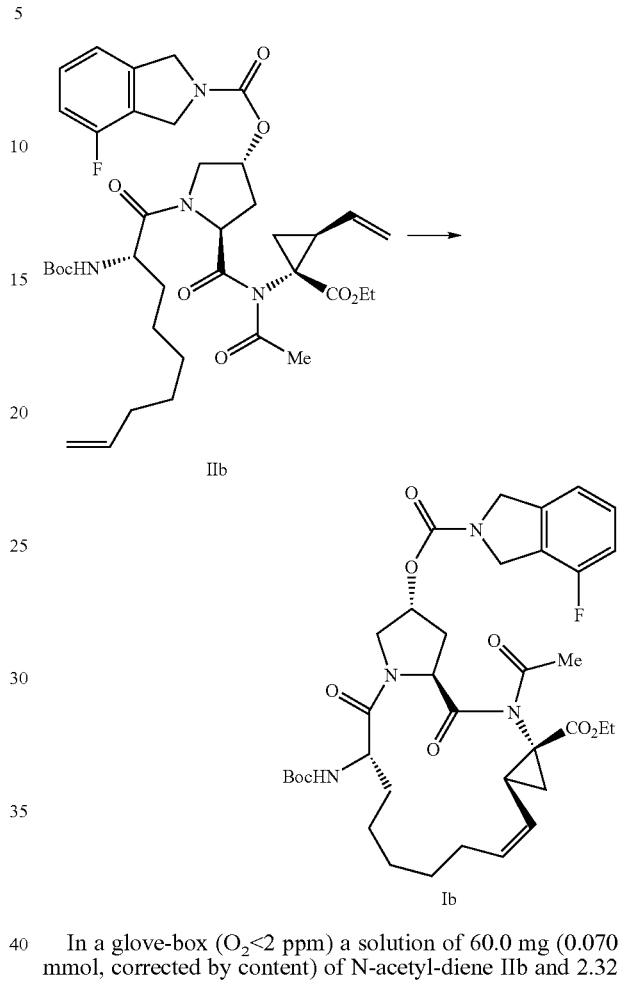

In a glove-box (O$_2$<2 ppm) a solution of 60.0 mg (0.070 mmol, corrected by content) of N-acetyl-diene IIb and 2.32 mg (0.0035 mmol) of catalyst 5024 in 1.7 mL of toluene (washed with aqueous hydrochloric acid and distilled under argon) was stirred at 60° C. in a 15 mL screw-capped flask. After 1.5 h one drop of ethylenediamine was added and the mixture was stirred for ca. 30 min outside of the glove box. After addition of 1 mL of 1 M aqueous solution of hydrochloric acid the biphasic mixture was stirred for ca. 5 min. A 0.5 mL aliquote of the organic phase was removed and evaporated to dryness; the oily residue was dissolved in 1 mL of acetonitrile and analyzed by HPLC. Conversion was 99.6 area %, the desired product (N-acetyl-RCM-ester Ib) had 89 area % purity.

HPLC method for the determination of conversion and selectivity: Waters XBridge C18 column, 4.6×150 mm, solvent A: water/acetonitrile 95/5, solvent B: acetonitrile, solvent C: buffer Bu$_4$N$^+$ HSO$_4^-$ pH 3 (1 g in 1 l water/acetonitrile 9:1), gradient from A/B/C 50/40/10 to 10/80/10 within 6.5 min, then 14 min isocratic, 40° C., 210 nm, 1 mL/min. Retention times: toluene 6.0 min, diene-acetate IIb 10.0 min, N-acetyl-RCM-ester Ib 8.65 min (identified by HPLC/MS, [MH]$^+$699.4 u), peaks of dimeric by-products at 13.3, 13.8 and 15.6 min (HPLC-MS: [MH]$^+$1396 and 1423 u). Only the sum of the dimer peaks is given in the tables and experiments.

Examples 2a-2o

The examples in Table 1 were carried out using the same procedure and conditions as in Example 1, but in the presence of various catalysts.

TABLE 1

| Reaction Nr. | Catalyst Nr. | N-Acetyl-Diene IIb (area %) | N-Acetyl-RCM-ester Ib (area %) | Dimers (area %) |
|---|---|---|---|---|
| 2a | 5000 | 4 | 53 | 3.2 |
| 2b | 5001 | 0.7 | 88 | 3.1 |
| 2c | 5002 | 2.9 | 49 | 3.1 |
| 2d | 5003 | 0.5 | 87 | 3.0 |
| 2e | 5006 | 5.6 | 51 | 4.4 |
| 2f | 5017 | <0.1 | 81 | 2.9 |
| 2g | 5025 | 11.3 | 61 | <0.1 |
| 2h | 5040 | 7.8 | 73 | 0.3 |
| 2i | 5041 | 3.4 | 55 | 5.1 |
| 2j | 5047 | 1.4 | 89 | 1.6 |
| 2k | 5055 | 0.4 | 91 | 3.7 |
| 2l | 5057 | 0.7 | 90 | 2.7 |
| 2m | 5059 | 0.6 | 92 | 2.8 |
| 2n | 5062 | 19 | 51 | <0.1 |
| 2o | 5065 | 0.5 | 89 | 3.0 |

Example 3

S/C 18

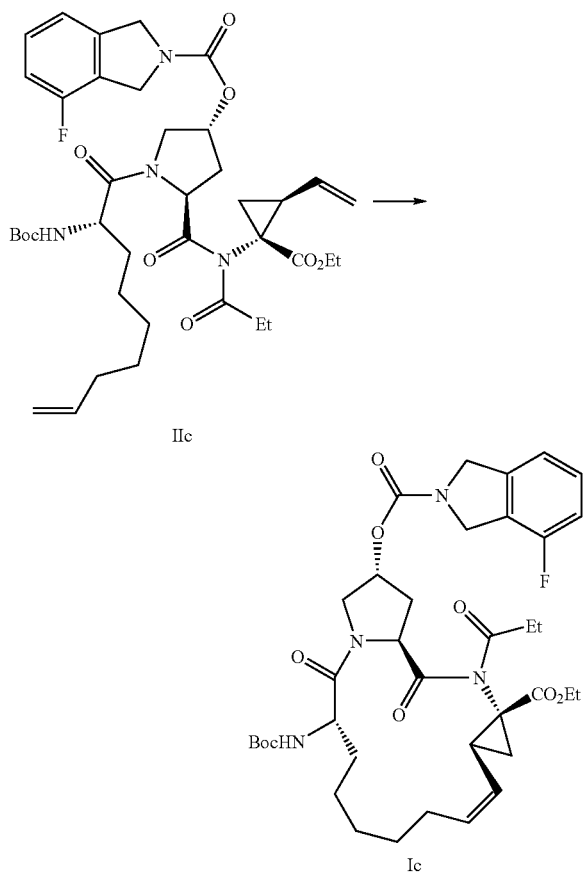

In a glove-box (O$_2$<2 ppm) a solution of 60.0 mg (0.070 mmol, corrected by content) of N-propionyl-diene IIc and 2.49 mg (0.0038 mmol) of catalyst 5024 in 1.7 mL of toluene (washed with aqueous hydrochloric acid and distilled under argon) was stirred at 60° C. in a 15 mL screw-capped flask. After 1.5 h one drop of ethylenediamine was added and the mixture was stirred for ca. 30 min outside of the glove box. After addition of 1 mL of 1 M aqueous solution of hydrochloric acid the biphasic mixture was stirred for ca. 5 min. A 0.5 mL aliquote of the organic phase was removed and evaporated to dryness; the oily residue was dissolved in 1 mL of acetonitrile and analyzed by HPLC. Conversion was >99.5 area %, the desired product (N-propionyl-RCM-ester Ic) had 86 area % purity.

HPLC method for the determination of conversion and selectivity: same as Example 1. Retention times: toluene 6.0 min, N-propionyl-diene IIc 10.7 min, N-propionyl-RCM-ester Ic 9.2 min (identified by HPLC/MS, [MH]$^+$713.3 u), peaks of dimeric by-product at 17.4 min.

MS: [MH]$^+$1426.6 u, peaks of unknown by-products at 12.3 min (MS: 768), 14.0 and 16.7 (complex MS spectrum); NMR: (δ, DMSO-D6, 120° C.): 1.07 (t, 3H), 1.14 (t, 3H), 1.23 (s, 9H), 1.26-1.48 (m, 6H), 1.71-1.80 (m, 1H), 1.84-1.90 (m, 2H), 1.96-2.03 (m, 1H), 2.11-2.23 (m, 2H), 2.34-2.44 (m, 1H), 2.61-2.68 (m, 2H), 2.70-2.82 (m, 1H), 3.86 (m, 1H), 4.02-4.22 (m, 5H), 4.66 (s, 4H), 5.08 (t, 1H), 5.30 (m, 2H), 5.49 (m, 1H), 6.22 (s, br, 1H), 7.03 (m, 1H), 7.12 (m, 1H), 7.31 (m, 1H); IR (selected absorptions, cm$^-$): 3286, 1711, 1627, 1523, 1366, 1249, 778.

Examples 4a-4o

The examples in Table 2 were carried out using the same procedure and conditions as in Example 3, but in the presence of various catalysts.

TABLE 2

| Reaction Nr. | Catalyst Nr. | N-Propionyl-Diene IIc (area %) | N-Propionyl-RCM-ester Ic (area %) | Dimers (area %) |
|---|---|---|---|---|
| 4a | 5000 | 19.6 | 27.0 | 2.4 |
| 4b | 5001 | <0.1 | 87.8 | 2.0 |
| 4c | 5002 | 18.9 | 26.9 | 2.4 |
| 4d | 5003 | <0.1 | 85.5 | 2.0 |
| 4e | 5006 | 18.6 | 22.8 | 1.5 |
| 4f | 5017 | 1.4 | 73.6 | 1.7 |
| 4g | 5025 | 35.6 | 10.7 | <0.1 |
| 4h | 5040 | 19.8 | 40.8 | <0.1 |
| 4i | 5041 | 8.9 | 37.9 | 4.1 |
| 4j | 5047 | 5.6 | 77.2 | 1.0 |
| 4k | 5055 | <0.1 | 86.9 | 2.1 |
| 4l | 5057 | <0.1 | 78.4 | 1.8 |
| 4m | 5059 | 0.3 | 81.5 | 2.3 |
| 4n | 5062 | 32.3 | 5.7 | <0.1 |
| 4o | 5065 | <0.1 | 83.7 | 1.9 |

Example 5

S/C 533, conc. ca 14%

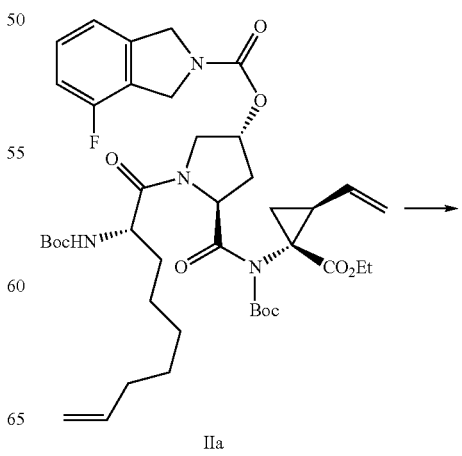

-continued

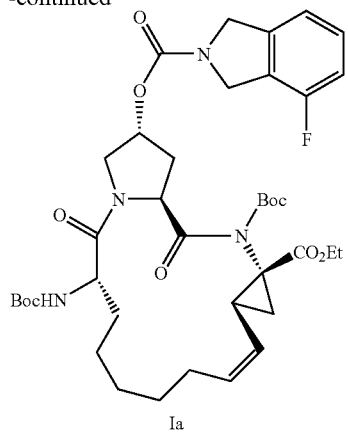

Ia

A solution of 15.7 g (20 mmol) of N-BOC-diene IIa in 115 mL of toluene was heated to 60° C. At this temperature 14.3 mg of catalyst 5024 dissolved in 5.9 mL of toluene was dosed within 1 h to the reaction mixture; an in process control showed complete conversion after dosing was completed (IIa n.d.). During the reaction the mixture was purged with nitrogen (150 mL/min). To the reaction mixture 118 mg of ethylene diamine was added. It was cooled to room, temperature and 40 mL of 0.5N aqueous HCl were added. The phases there separated and the aqueous layer was extracted with 100 mL of toluene. The combined organic layers were washed with brine, dried over sodium sulfate, filtered and concentrated to dryness to obtain 18.5 g of raw product. Purification was achieved by column chromatography (silica gel 0.040-0.063 mm) with a mixture of hexane and ethyl acetate using a gradient of 8:2 then 7:3 and 6:4. Fractions containing the desired product in comparable purity were collected, concentrated and recrystallized from ethyl acetate. Drying under reduced pressure afforded 11.6 g of colorless crystals (98.6 area % HPLC) and 2.9 g of residue from concentrated mother liquor (95.5 area % HPLC) giving a yield of 93%.

HRMS, $[MH]^+$757.38174; NMR (selected peaks, δ, DMS-D6, 120° C.): 1.15 (t, 3H), 1.24 (s, 9H), 1.29-1.46 (m, 6H), 1.49 (s, 9H), 1.62 (m, 1H), 1.73 (m, 2H), 1.99-2.24 (m, 4H), 2.50-2.60 (m, 2H), 3.87 (m, 1H), 4.06 (q, 2H), 4.17 (m, 2H), 4.67 (s, 4H), 5.20 (m, 1H), 5.30 (m, 1H), 5.33 (m, 1H), 5.46 (m, 1H), 6.20 (d, br, 1H), 7.03 (m, 1H), 7.12 (d, 1H), 7.31 (m, 1H); IR (selected absorptions, $cm^{-1}$): 3361, 1739, 1692, 1519, 1370, 1175, 792.

Example 6

S/C 1000, conc.=8%

A solution of 5.00 g (6.67 mmol) of N-acetyl-diene IIb in 70 mL of toluene was extracted twice with 15 mL HCl 0.5 mol/l and rotary concentrated to a total weight of 40.2 g (corresponds to a 8% weight/weight concentration). To this solution was added at 70° C. under vacuum (pressure=ca. 0.26 bar) by dropping funnel a solution of 4.75 mg (0.0067 mmol) of catalyst 5058 in 10 mL of toluene. The catalyst was added during 1 h. Under these conditions a small amount of toluene (ca 10 mL) distilled off in the course of the reaction. After 1.5 h of total reaction time 23 μl (0.34 mmol) of ethylenediamine were added at ambient pressure, the reaction mixture was concentrated under vacuum, washed with 0.5 M aqueous solution of hydrochloric acid, treated with 10 mL ethyl acetate and 0.41 g of charcoal and stirred for 30 min, filtered and evaporated to dryness. N-acetyl-RCM-ester Ib was isolated as yellow foam (5.07 g).

HPLC analysis showed Ib (89.2 area %), 0.2 area % IIb and 7.7 area % dimers (identified by HPLC/MS). The content by HPLC with internal standard was 83.5%, which corresponds to 90.8% yield.

HPLC method for content determination: Gemini $C_6$-Phenol colum, 4.6×150 mm, 3.0 um, solvent A: water/acetonitrile 95/5, solvent B: buffer $Bu^4N^+HSO_4^-$pH 3 (1 g in 1 l water/acetonitrile 9:1); solvent C: acetonitrile gradient from A/B/C 25/5/70 to 15/5/80 within 1.0 min, then 4 min isocratic, 45° C., 210 nm, 2.3 mL/min. Retention times: N-acetyl-diene IIb 1.88 min, N-acetyl-RCM Ib 2.18 min, int. standard dinitrobenzene (1 g/l acetonitrile) 10.3 min.

MS: $[MH]^+$699.4; NMR (selected peaks, δ, $CDCl_3$): ($CH_3C=O$) 2.27 (s, 3H), ($CH_3$—$CH_2$) 1.23 (t, 3H), ($CH_3$—$\overline{CH_2}$) 4.14 and 4.22 (m, 1H each), (t-Bu) 1.27 (s, 9H); IR: carbonyl absorption at 1705 $cm^{-1}$ (strong, broad).

Example 7

S/C 600, conc.=1%

To a solution of 1.0 g (1.35 mmol) of N-acetyl-diene IIb in 114 mL of toluene was added at 70° C. under vacuum (pressure=ca. 0.26 bar) by dropping funnel a solution of 1.63 mg (0.0017 mmol) of catalyst 5058 in 4 mL of toluene. The catalyst was added during 1 h. Under these conditions a small amount of toluene (ca 14 mL) distilled off in the course of the reaction. After 2 h of total reaction time 10 μl (0.15 mmol) of ethylenediamine were added at ambient pressure, the reaction mixture was concentrated under vacuum, washed with 0.5 M aqueous solution of hydrochloric acid, stirred with 80 mg of charcoal for 30 min, filtered and evaporated to dryness. N-acetyl-RCM-ester Ib was isolated as white foam (1.07 g).

HPLC analysis showed 2.2 area % toluene, 91.9 area % Ib, 1.5 area % IIb and 1.0 area % dirners. The purity by HPLC with internal standard was 89.0% content, which corresponds to 98% yield.

Examples 8a-8e

The experiments in Table 4 have been carried out in analogy to Example 7, Catalyst No., temperature, reaction time, yield and purity of N-acetyl-RCM ester Ib are given in the table.

TABLE 3

| Reaction Nr. | Catalyst No. | T ° C. | N-acetyl-Diene IIb a % | N-acetyl-RCM-ester Ib a %/% y. | Dimers a % |
|---|---|---|---|---|---|
| 8a | 5065 | 70 | 1.5 | 87/95 | 7.5 |
| 8b | 5008 | 70 | 3.3 | 87/92 | 7.2 |
| 8c | 5024 | 70 | 1.5 | 88/95 | 6.7 |
| 8d | 5064 | 70 | 1.4 | 87/95 | 7.7 |
| 8e$ | 5065 | 70 | 1.8 | 84/89 | 9.1 |

All reactions were run at S/C 1000 on a 7.0 mmol scale for 1.5 h.
Concentration is 8%.
% y. = % yield determined by HPLC with internal standard;
a %: HPLC area %.
$12% concentration.

Example 9

S/C 1000, conc.=8%

To a solution of 5.83 g (7.00 mmol) of N-propionyl-diene IIc in 80 mL of toluene was added at 70° C. under vacuum (pressure=ca. 0.26 bar) by dropping funnel a solution of 5.26 mg (0.0070 mmol) of catalyst 5065 in 15 mL of toluene. The catalyst was added during 1 h, then the dropping funnel was rinsed with 15 mL of toluene. Under these conditions a small amount of toluene (ca 10 mL) distilled off in the course of the reaction. After 1.5 h of total reaction time 24 µl (0.35 mmol) of ethylenediamine were added at ambient pressure, the reaction mixture was concentrated under vacuum, washed with 0.5 M aqueous solution of hydrochloric acid, treated with 10 mL dichloromethane and 0.50 g of charcoal and stirred for 30 min, filtered and evaporated to dryness. N-propionyl-RCM-ester Ic was isolated as an off-white foam (5.96 g).

HPLC analysis showed Ic (80.4 area %), IIc (2.4 area %) and dimers (4.8 area %, identified by HPLC/MS). The content by HPLC with internal standard was 74.5%, which corresponds to 89% yield. The crude product could be purified, if desired, by column chromatography on silica gel, eluent heptane/ethyl acetate. MS: [MH]$^+$713.3.

HPLC method for content determination: Gemini C6-Phenol colum, 4.6×150 mm, 3.0 um, solvent A: water/acetonitrile 95/5, solvent B: buffer $Bu_4N^+HSO_4^-$ pH 3 (1 g in 1 l water/acetonitrile 9:1); solvent C: acetonitrile gradient from A/B/C 25/5/70 to 15/5/80 within 1.0 min, then 4 min isocratic, 50° C., 210 nm, 2.3 mL/min. Retention times: N-propionyl-diene IIc 1.93 min, N-propionyl-RCM-ester Ic 2.07 min, int. standard dinitrobenzene (1 g/l acetonitrile) 1.03 min.

Example 10

S/C 20

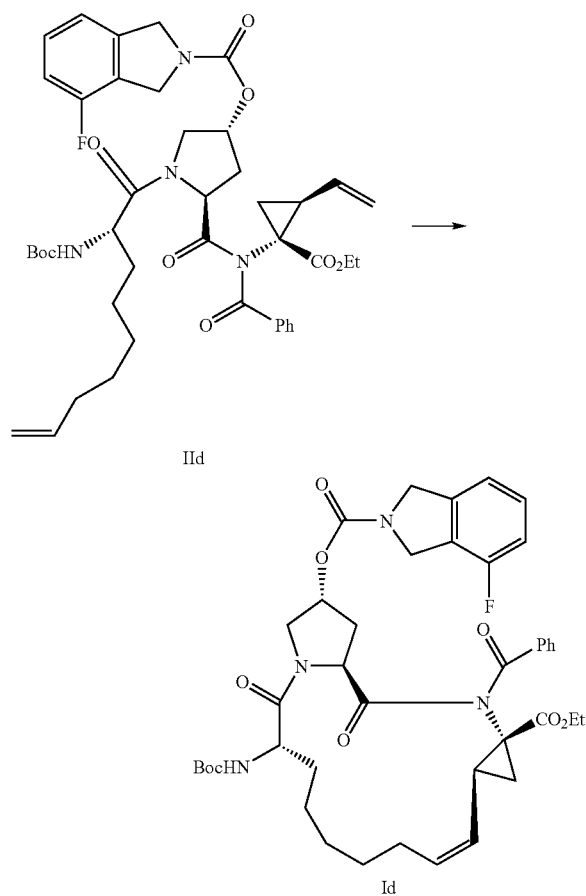

In a glove-box (O$_2$<2 ppm) a solution of 60.0 mg (0.073 mmol, corrected by content) of N-benzoyl-diene IId and 2.40 mg (0.0038 mmol) of catalyst 5024 in 1.7 mL of toluene (washed with aqueous hydrochloric acid and distilled under argon) was stirred at 60° C. in a 15 mL screw-capped flask. After 1.5 h two drops of ethyl vinylether were added and the mixture was stirred for ca. 30 min outside of the glove box. After addition of 1 mL of 1 M aqueous solution of hydrochloric acid the biphasic mixture was stirred for ca. 5 min. A 0.5 mL aliquote of the organic phase was removed and evaporated to dryness; the oily residue was dissolved in 1 mL of acetonitrile and analyzed by HPLC. Conversion was 99 area %, the desired product (N-benzoyl-RCM-ester Id) had 83 area % purity.

HPLC method for the determination of conversion and selectivity: Gemini C6 Phenyl (by Phenomena, Torrance Calif., USA), 4.6×150 mm, solvent A: water/acetonitrile 95/5, solvent B: acetonitrile, solvent C: buffer $Bu_4N^+HSO_4^+$ pH 3 (1 g in 1 l water/acetonitrile 9:1), gradient from A/B/C 45/50/5 to 10/85/5 within 7.0 min, then 5 min isocratic, 50° C., 210 nm, 2 mL/min. Retention times: toluene 2.5 min, diene-benzoate Id 6.62 min, N-benzoyl-RCM-ester Id 5.96 min (identified by HPLC/MS, [M-H]$^+$761.2 u), peaks of dimeric by-products at 6.5 to 9.1 min (HPLC-MS: [M-H]$^+$ 1520 and 1576 u). Only the sum of the dimer peaks is given in the tables and experiments: MS: [MH]$^+$761.2 u; NMR: (δ, CDCl3, selected peaks): 1.25 (t. 3H), 1.34 (d, 9H)

Example 11

The examples in Table 4 were carried out using the same procedure and conditions as in Example 10, but in the presence of various catalysts.

TABLE 4

| Reaction Nr. | Catalyst Nr. | N-Benzoyl-Diene IId (area %) | N-Benzoyl-RCM-Ester Id (area %) | Dimers (area %) |
| --- | --- | --- | --- | --- |
| 11a | 5000 | 19 | 52 | 16 |
| 11b | 5001 | 1 | 90 | 5 |
| 11c | 5002 | 22 | 47 | 13 |
| 11d | 5003 | <1 | 89 | 5 |
| 11e | 5006 | 30 | 48 | 20 |
| 11f | 5017 | 4 | 78 | 10 |
| 11g | 5025 | 63 | 26 | 5 |
| 11h | 5040 | 17 | 75 | 5 |
| 11i | 5041 | 17 | 61 | 19 |
| 11j | 5047 | 7 | 78 | 7 |
| 11k | 5055 | 1 | 86 | 8 |
| 11l | 5057 | 15 | 72 | 8 |
| 11m | 5059 | 4 | 83 | 6 |
| 11n | 5062 | 56 | 34 | 7 |
| 11o | 5065 | <1 | 84 | 7 |

Example 12

S/C 135

To a solution of 3.29 g (4.00 mmol) of N-benzoyl-diene IId (96% purity) in 44 mL of toluene was added under argon bubbling (33 mL/min) at 60° C. 21.3 mg (0.03 mmol) of catalyst 5065. After 4.5 h stirring at this temperature 97 µl of ethyl vinylether were added followed by 67 µl (1.0 mmol) of ethylenediamine and the mixture was stirred at room temperature for 10 min. After this time the mixture was extracted with 1 M aqueous solution of hydrochloric acid and with water. The organic phase was treated with decolorizing charcoal, filtered and evaporated to dryness to afford 3.2 g of N-benzoyl-RCM-ester Id as a light brown solid. Crystallization of the crude product from ethanol afforded the desired Id (2.46 g, 81%) as an off-white crystalline solid with 93% purity.

Example 13

S/C 135

The examples in Table 5 were carried out using the same procedure and conditions as in Example 12, but in the presence of various catalysts.

TABLE 5

| Reaction Nr. | Catalyst Nr. | RP column | | |
|---|---|---|---|---|
| | | N-Benzoyl-Diene IId a % | N-Benzoyl-RCM-Ester Id a % | Dimers a % |
| 13a | 5058 | 20 | 64 | 13.6 |
| 13b | 5064 | 15 | 69 | 13.2 |
| 13c | 5072 | 35 | 50 | 13.0 |
| 13d | 5073 | 0.5 | 84 | 10.6 | a %: HPLC area %.

Example 14

S/C 2000, conc.=8%

To a solution of 6.57 g (8.00 mmol) of N-benzoyl-diene IId in 93 mL of toluene was added at 70° C. under vacuum (pressure=ca. 0.26 bar) by dropping funnel a solution of 2.78 mg (0.0039 mmol) of catalyst 5065 in 10 mL of toluene. The catalyst was added during 1 h. Under these conditions a small amount of toluene (ca 10 mL) distilled off in the course of the reaction. After 1.5 h of total reaction time 20 µl (0.20 mmol) of ethyl vinylether were added at ambient pressure followed after 1 h by 14 µl (0.20 mmol) of ethylenediamine and the reaction mixture was concentrated under vacuum. After addition of 10 mL of dichloromethane the solution was washed with 0.5 M aqueous solution of hydrochloric acid, treated with 5 mL of dichloromethane and evaporated to dryness. N-benzoyl-RCM-ester Id was isolated as a light tan solid (7.05 g). HPLC analysis showed 84.3 area % Id, 1.42 area % IId and 10.3 area % dimers. The content by HPLC with internal standard was 70.3%, which corresponds to 81.5% yield.

Example 15

Saponification of Id

A suspension of 6.52 g (6.75 mmol) N-benzoyl-RCM-ester Id in 25 mL of THF, 25 mL of ethanol and 5 mL of water was cooled to 0° C. At an internal temperature of 0.7° C. to 4.0° C. a solution of 4.0 g (98.01 mmol) sodium hydroxide in 20 mL of water was added within 22 min. The mixture was stirred for 16.5 h at 0° C. At this temperature 12.9 mL (98.96 mmol) aqueous HCl 25% was added. The mixture was concentrated at 45° C./45 mbar to a residual weight of ca. 30 g. To the suspension 5 mL of water was added and extracted with 30 mL of dichloromethane. The organic layer was washed with 25 mL of water and the combined aqueous layers were extracted with 25 mL of dichloromethane. The combined organic layers there concentrated to a residual volume of 15 mL at 60° C./900 mbar. To the concentrate 50 mL of THF is added slowly and again concentrated to a residual weight of ca. 40 g at 60° C./700 mbar). Seeds were added and the suspension was stirred 1 h at room temperature and 1.5 h at 0° C. to complete the crystallization. The crystals were collected on a filter nutsche and washed with 12 mL of THF (precooled to –20° C.). The crystals were dried for 5 h at 50° C./10 mbar. 3.55 g of XXb with a purity of 97.2% (yield 81.3%) were obtained.

Example 16

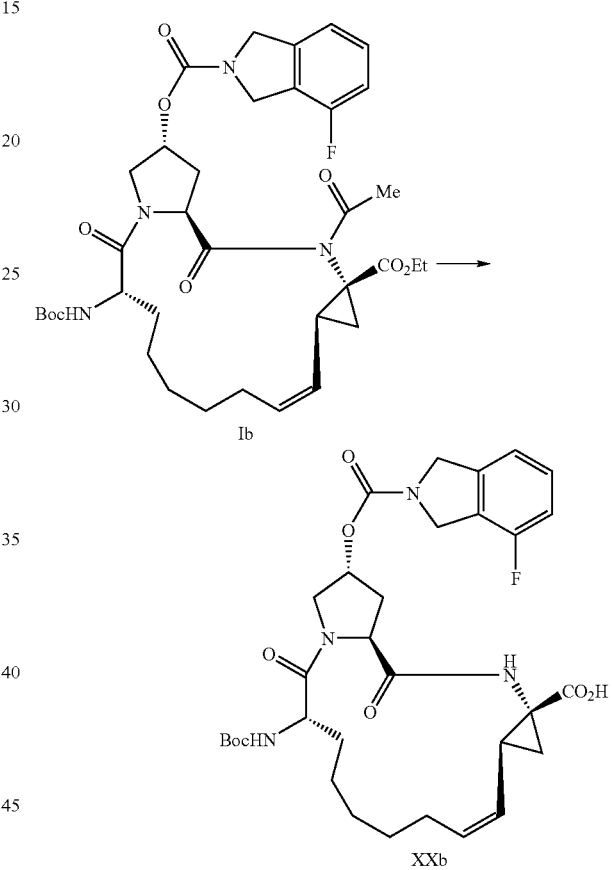

To a solution of the N-acetyl-RCM-ester Ib (2.41 g, 2.88 mmol, 83.5% content) in 20 mL of ethanol was added under argon at ca. 3° C. (ice bath) a solution of sodium hydroxide (1.50 g, 36.7 mmol) in water (6.5 mL). The solution was stirred at 5-10° C. for 6 h, and then treated with 37% HCl (4.5 mL) at ca. 3° C. The resulting suspension was concentrated and extracted with a mixture of dichloromethane (15 mL) and water (8 mL). The organic phase was evaporated, the oily residue was taken up in THF (25 mL). The resulting suspension was concentrated to a total weight of 12.6 g, stirred for 1 h at 55° C. and in an ice bath for 3 h. The precipitate was filtered off, washed with cold THF and dried to constant weight (40° C./5 mbar/3 h) to afford 1.64 g of carboxylic acid XXb as a white solid with 97 area % according to HPLC and 89.2% content. Total content of dimers: 0.9%:

MS: [MH]$^+$627.3; IR: carbonyl absorption at 1706 cm$^{-1}$ (strong, broad) and 1680 cm$^{-1}$ (medium, sharp).

Example 17

Telescoped Process for the Preparation of XXb

A suspension of 90.2 g (191 mmol) (S)-2-tert-butoxycarbonylamino-non-8-enoic acid dicyclohexylammonium salt (commercially available from Synthetech Oreg., USA) in 373 g of THF was cooled to −5° C. and 22.7 g (188 mmol) pivaloyl chloride was added within 30 min. The mixture was stirred for 1.5 h at 0° C. At 5-10° C. 75.0 g (174 mmol) 4-fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester (XIV) was added in five portions followed by 18 g THF. The suspension was heated to 20-25° C. and stirred for 4 h. After complete conversion 225 g of water was added and the solvent was removed at 50° C. under reduced pressure. To the residue 649 g of toluene was added and the internal temperature was decreased to 20-25° C. To the suspension 80 g water and 8.57 g (87 mmol) 37% aqueous hydrochloric acid was added. The precipitated dicyclohexylammonium hydrochloride was removed by filtration and the filter cake was washed with 114 g toluene. To the filtrate 26 g toluene was added and phases were separated. The organic phase was treated at 20-25° C. with a mixture of 267 g of water, 43.0 g (301 mmol) of 28% aqueous sodium hydroxide and 2.11 g (35 mmol) of ethylene diamine for 30 min. Then the phases were separated and the organic layer was washed with a mixture of 267 g of water and 21.5 g (151 mmol) of 28% aqueous sodium hydroxide. The organic phase was concentrated at 65° C. under reduced pressure to a residual volume of 500 mL. The solution was cooled to −3° C. and 27.5 g (196 mmol) benzoyl chloride was added. Then 84.6 mL (188 mmol) lithium tert-butoxide in THF was dosed within 1 h. After additional stirring for 15 min a sample showed conversions typically to be <3% of diene XV. The mixture was heated to 20-25° C. and diluted with 337 g toluene. The solution was first washed with a mixture of 210 g of water and 33.5 g (235 mmol) of 28% aqueous sodium hydroxide, then with a mixture of 210 g of water and 16.8 g (118 mmol) of 28% aqueous sodium hydroxide and finally with a mixture of 210 g of water and 11.6 g (117 mmol) of 37% aqueous hydrochloric acid. The organic phase was then dried by concentrating to a residual volume of 650 mL at 65° C. under reduced pressure. To the residue 865 g toluene were added and the solution was heated to 75° C. jacket temperature. The pressure was reduced to 290-330 mbar and 167 mg (0.235 mmol) of catalyst 5065 dissolved in 35 g toluene and 13 g dichloromethane was added within 30 min. After stirring for additional 15 min a sample showed conversions typically to be <3% N-benzoyl-diene IId. Then 0.5 g water was added and the mixture was stirred for 10 min. The mixture was concentrated to a residual volume of 200 mL at 75° C. and reduced pressure, 415 g THF and 496 g ethanol were added. The internal temperature was decreased to 20-25° C. and 106 g water was added. The suspension was cooled to 0-5° C. and 340 g (2.38 mol) of 28% aqueous sodium hydroxide was added. The internal temperature was raised to 7-10° C. and the reaction mixture was stirred for 9-11 h. After this time the conversion was typically <1% N-benzoyl-RCM-ester Id. At an internal temperature of 5-10° C. 237 g (2.40 mol) of 37% aqueous hydrochloric acid was added. The internal temperature was raised to 40° C. and the suspension was concentrated to 700 mL under reduced pressure. At an internal temperature of 30-35° C. 108 g water and 620 g dichloromethane were added. The phases were separated and the aqueous phase was extracted with 124 g dichloromethane. The combined organic phases were washed with 94 g of water and the aqueous phase was back-extracted with 102 g of dichloromethane. The combined organic phases were concentrated to a residual volume of 300 mL at a jacket temperature of 80° C. To the residue 899 g THF were dosed, first an amount that gave a reactor volume of 470 mL and after adding seeds, in such a rate the residual volume of 470 mL could be maintained during continued distillation. After all the THF had been added the internal temperature was decreased to 0-3° C. within 1.5 h. The crystals were collected on a filter nutsche and washed with 115 g of THF. The product was dried for 3-6 h at 30° C./15 mbar. 79.2 g of colorless crystals of XXb were obtained in an assay of 89% wt which corresponds to a yield of 64%.

Example 18

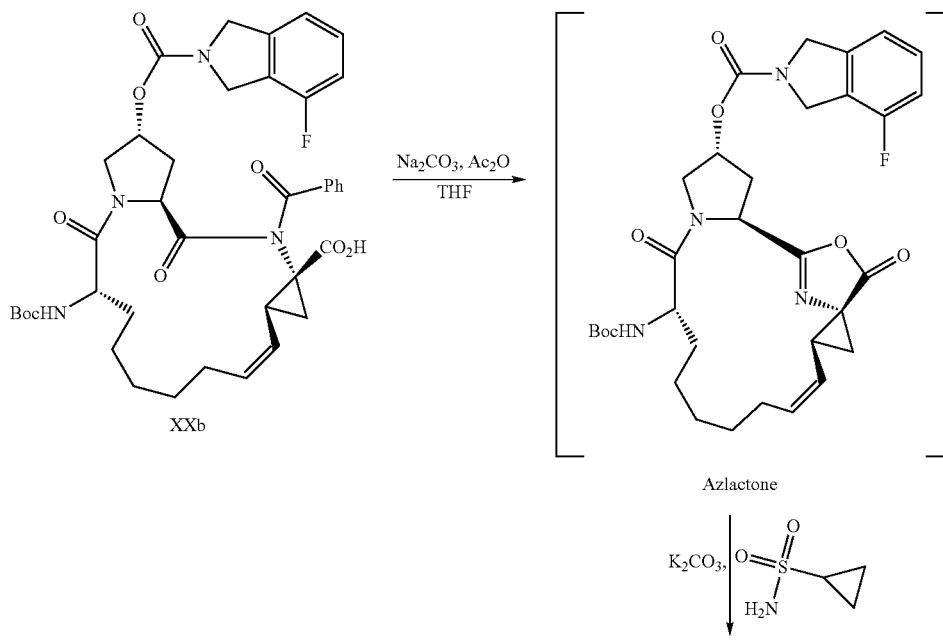

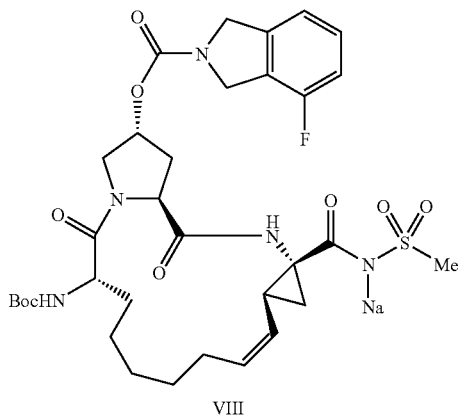 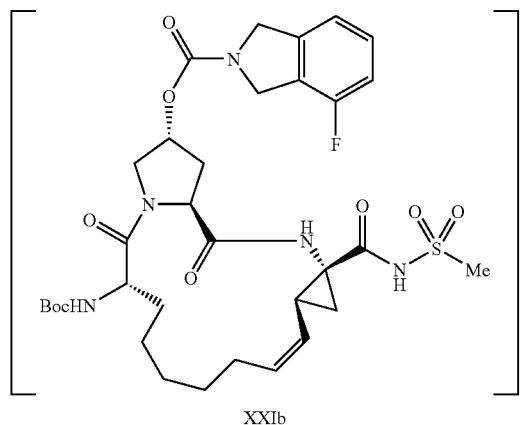

VIII    XXIb

Preparation of sodium ((2R,6S,13aS,14aR,16aS,Z)-6-(tert-butoxycarbonylamino)-2-(4-fluoroisoindoline-2-carbonyloxy)-5,16-dioxo-1,2,3,5,6,7,8,9,10,11,13a,15,16a-hexadecahydrocyclopropa[e]pyrrolo[1,2-a][1,4]di-aza-cyclopentadecine-14a-carbonyl) (cyclopropylsulfonyl) amide (HCV protease inhibitor; compound XXIIb).

To a suspension of 30.0 g (0.043 mol) of carboxylic acid (product of example 11 with an assay of 90.2%(m/m)) and 14.0 g of sodium carbonate in 225 g of tetrahydrofuran was added at 45° C. within 30 minutes 7.60 g (0.074 mol) of acetic acid anhydride and the resulting mixture was stirred at 45° C. for 8 hours. To the resulting suspension was then added 30.2 g (0.17 mol) of potassium carbonate and 8.0 g (0.065 mol) of cyclopropylsulfonamide. The mixture was heated to 62° C. and stirred at this temperature for 17 hours. The mixture was concentrated to a residual volume of 200 mL and then treated with 200 g of water. The biphasic mixture was stirred for 15 minutes and the layers were then allowed to separate. The lower aqueous phase was removed. The organic phase was diluted with 90 g of ethyl acetate and washed with 3% sulfuric acid (1×140 g) and water (3×130 g). The organic layer was concentrated to dryness and then diluted with 400 mL of ethyl acetate. Residual amounts of water were removed by a continuous azeotropic distillation with ethyl acetate. The mixture was then treated at 10° C. with 20 mL of methanol, followed by 10.0 g of sodium methylate (30% in methanol). From the resulting mixture approx. 300 mL of ethyl acetate/methanol were then distilled off. The mixture was then treated at 34° C. within one hour with 300 mL of ethyl acetate and 5 g of water. The resulting mixture was allowed to cool to ambient temperature within 4 hours. The crystals were filtered off, washed with 80 mL of ethyl acetate and dried at 80° C./<30 mbar for 20 hours to afford 30.4 g (87% corrected yield) of the title compound as white crystals with an assay of 92.7%(m/m):

MS: 732.28 (M$^+$+H), 676.23, 632.25; $^1$H-NMR (400 MHz, DMSO-d$_6$): 7.89-7.80 (m, 1H), 7.39-7.31 (m, 1H), 7.21-7.06 (m, 2H), 6.97-6.90 (m, 1H), 5.49-4.41 (m, 1H), 5.31-5.21 (m, 2H), 4.66 (s, br, 4H), 4.45-4.35 (m, 1H), 4.19-4.08 (m, 2H), 3.91-3.81 (m, 1H), 2.68-2.58 (m, 1H), 2.30-2.14 (m, 3H), 2.0-1.2 (m, 12H), 1.17 and 1.14 (2s, 9H), 0.78-0.69 (m, 2H), 0.62-0.53 (m, 2H).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A process for the manufacture of a macrocyclic compound of formula XXII comprising

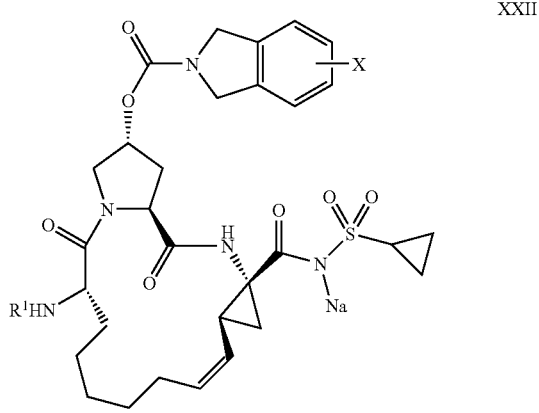

XXII the steps of (a) of subjecting a diene of formula II to a ring closing metathesis in the presence of a ruthenium (II) carbene complex to form a macrocyclic ester of formula I wherein: R$^1$ is

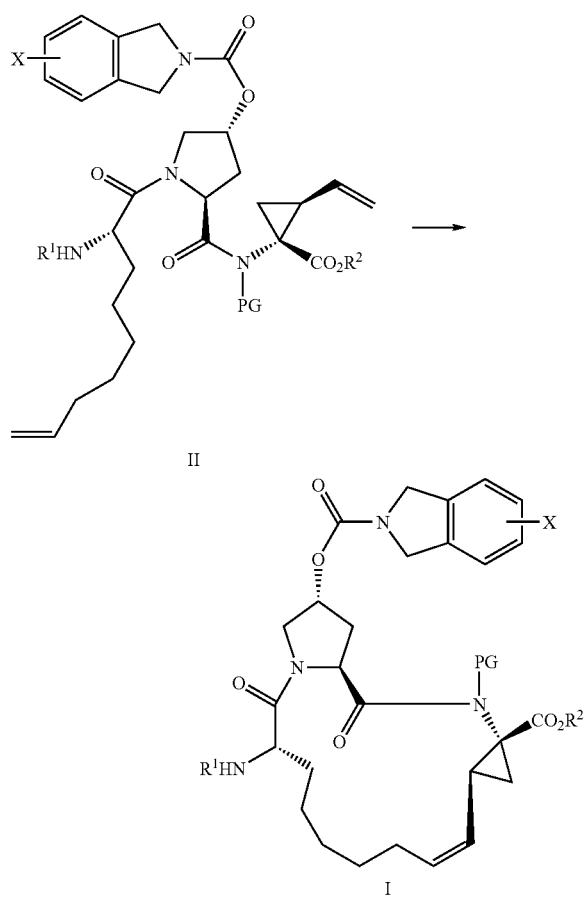

II

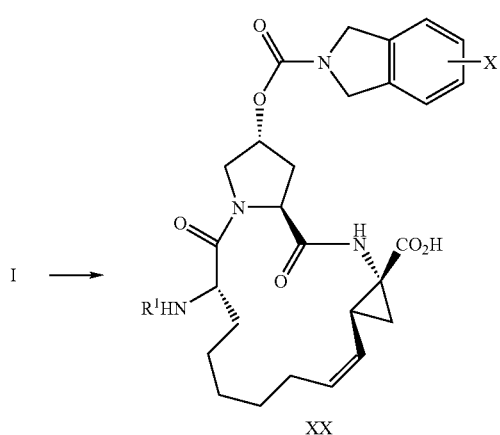

I an amino protecting group, $R^2$ is $C_{1-4}$-alkyl and X is halogen to a ring closing metathesis reaction in the presence of a ruthenium (II) carbene complex; (b) hydrolyzing the macrocyclic ester of formula I and removing the protecting group PG to form the

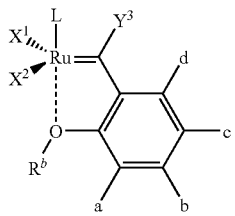

XX macrocyclic acid of the formula XX wherein $R^1$ is an amino protecting group and X is halogen;

c) contacting XX with cyclopropyl sulfonamide to form the macrocyclic sulfonamide of formula XXI wherein $R^1$ is an amino protecting group and X is halogen; and,

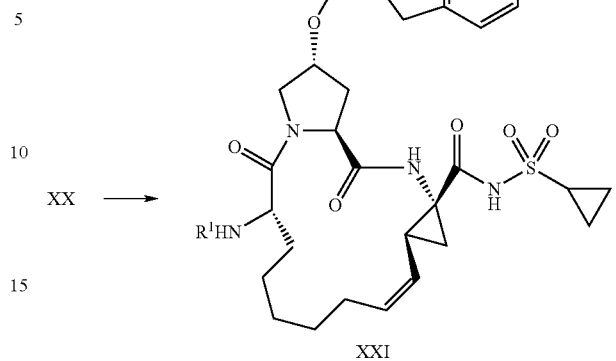

XXI d) treating the macrocyclic sulfonamide of formula XXI with a sodium base to form the macrocyclic compound of formula XXII.

2. A process according to claim 1 wherein the ruthenium (II) carbine complex is selected from the group consisting of IIa, IIb, IIIc, IIId, IIIe, IIIf, IIIg and IIIh:

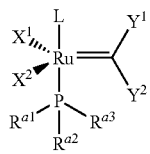
IIIa

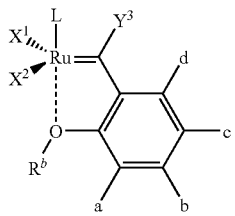
IIIb

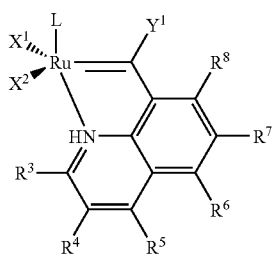
IIIc

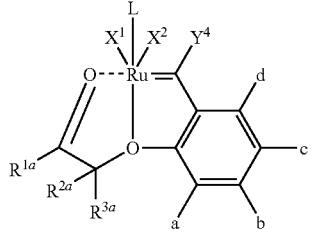
IIId

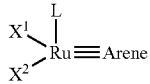
IIIe

-continued

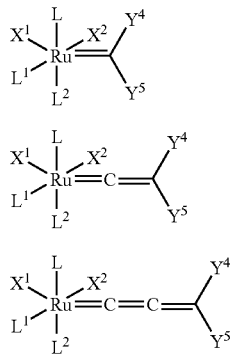

wherein:

L, $L^1$ and $L^2$ are neutral ligands;

$X^1$ and $X^2$ are independently anionic ligands;

$Y^1$ and $Y^2$ are (i) independently of each other hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl, $C_{1-6}$-alkylsulfinyl, or (ii) $Y^1$ and $Y^2$ along with the carbon to which they are attached are a cycle VIa wherein G is hydrogen or aryl; or

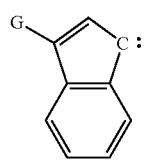

(iii) $Y^1$ and $Y^2$ along with the carbon to which they are attached are a cumulens VIa or VIc

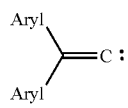

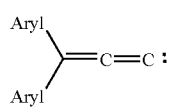

$Y^3$ is hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl, $C_{1-6}$-alkylsulfinyl;

$Y^4$ and $Y^5$ independently of each other is hydrogen, $C_{1-6}$-alkyl, $C_{3-8}$-cycloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, aryloxy, $C_{1-6}$-alkoxycarbonyl, $C_{1-6}$-alkylthio, aryl, arylthio, $C_{1-6}$-alkylsulfonyl, $C_{1-6}$-alkylsulfinyl;

$R^{a1} R^{a2}$ and $R^{a3}$ independently of each other are $C_{1-6}$-alkyl, $C_{3-7}$-cycloalkyl, aryl, heteroaryl or $R^{a1}$ and $R^{a2}$ or $R^{a2}$ and $R^{a3}$ or $R^{a1}$ and $R^{a3}$ form together a 1,5-bridged cyclooctyl group;

$R^b$ is $C_{1-6}$-alkyl $C_{2-6}$-alkenyl, halogen-$C_{1-6}$-alkyl, $C_{2-6}$-alkynyl, aryl, $C_{1-6}$-alkoxycarbonyl, $C_{1-6}$-alkylcarbonyl, mono-$C_{1-6}$-alkyl- or di-$C_{1-6}$-alkylamino, $C_{1-6}$-alkylaminocarbonyl, $C_{1-6}$-alkylthiocarbonyl, $C_{1-6}$-alkylsulfonyl, $C_{1-6}$-alkylsulfinyl or arylalkyl;

$R^3$, $R^4$, $R^5$, $R^6$, $R^7$ and $R^8$ independently of each other have the meaning of hydrogen, $C_{1-6}$-alkyl, $C_{1-6}$ haloalkyl, $C_{2-6}$-alkenyl, $C_{2-6}$-alkynyl, $C_{1-6}$ haloalkyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$ haloalkyl sulfonyl amino, $SO_3$—$C_{1-6}$-alkyl or $OSi(C_{1-6}$-alkyl$)_3$ and $SO_2$—NR'R" wherein R' and R" (i) independently of each other have the meaning of hydrogen, aryl or $C_{1-6}$-alkyl or (ii) R' and R" together with the N atom form a carbocycle;

a, b, c and d are independently hydrogen, $C_{1-6}$-alkyl, $C_{1-6}$ haloalkyl, $C_{2-6}$-alkenyl, $C_{2-6}$-alkynyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, $C_{1-6}$ haloalkyl sulfonyl amino, $SO_3$—$C_{1-6}$-alkyl, $OSi(C_{1-6}$-alkyl$)_3$ or $SO_2NR'R"$ wherein R' and R" (i) are independently hydrogen, aryl or $C_{1-6}$-alkyl or (ii) R' and R" together with the N atom to which they are attached form a carbocycle;

Arene is phenyl or naphthyl optionally mono-, di-, tri- or multiply-substituted by halogen, hydroxy, cyano, $C_{1-6}$ haloalkyl, $NO_2$, amino, mono-$C_{1-6}$-alkyl- or di-$C_{1-6}$-alkylamino, carboxy, aminocarbonyl, $C_{1-6}$-alkyl, $C_{1-6}$-alkoxy, $C_{1-6}$-alkylcarbonyl, $C_{1-6}$-alkylsulfonyl, aryl, aryloxy $SO_2$-aryl, $SO_3H$, $SO_3$—$C_{1-6}$-alkyl, $SO_2$—NR'R" wherein R' and R" independently of each other are hydrogen or $C_{1-6}$-alkyl;

$R^{1a}$ is hydrogen, hydroxy, $C_{1-6}$-alkyl, $C_{1-6}$-alkoxy, $C_{2-6}$-alkenyloxy, $C_{3-8}$-cycloalkyloxy, halogen-$C_{1-6}$-alkyloxy, aryl, aryloxy, $C_{1-6}$-alkylthio, arylthio, or —NR'R" wherein R' and R" (i) independently of each other are hydrogen, $C_{1-6}$-alkyl, $C_{3-8}$-cycloalkyl, aryl, aryl-$C_{1-6}$-alkyl or (ii) R' and R" together with the N atom to which they are attached form a 5 to 8 member carbocycle which may contain nitrogen, oxygen or sulfur as additional hetero atom;

$R^{2a}$ and $R^{3a}$ are independently of each other H, $C_{1-6}$-alkyl, $C_{3-8}$-cycloalkyl, aryl, $C_{7-18}$-arylalkyl or $R^{1a}$ and $R^{2a}$ or $R^{1a}$ together form a 5 to 12 member carbocycle.

3. A process according to claim 2 wherein L is VII, VIII, IX or XVII wherein;

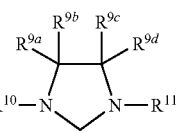

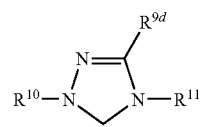

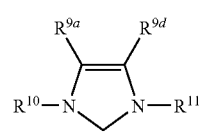

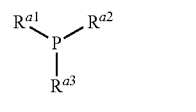

$R^{10}$ and $R^{11}$ are independently $C_{1-6}$-alkyl, aryl, $C_{2-6}$-alkenyl or 1-adamantyl and $R^{9a-d}$ are (i) independently hydrogen, $C_{1-6}$-alkyl, $C_{2-6}$-alkenyl or aryl, or (ii) $R^{9b}$ and $R^{9c}$ or $R^{9a}$ and $R^{9d}$ taken together form a $(CH_2)_4$ bridge; or, (iii) $R^{9a}$ and $R^{9d}$ in formula IX both are halogen;

$R^{a1-a3}$ are (i) independently $C_{1-6}$-alkyl, $C_{3-7}$-cycloalkyl, aryl, heteroaryl or (ii) $R^{a1}$ and $R^{a2}$ or $R^{a2}$ and $R^{a3}$ or $R^{a1}$ and $R^{a3}$ together form together a 1,5-bridged cyclooctyl group.

4. A process according to claim 3 wherein $X^1$ and $X^2$ are a halogenide or a pseudo halogenide.

5. A process according to claim 2 wherein the ruthenium (II) carbine complex is selected from the group consisting of IIa, IIb, IIIc, IIId, IIIf, IIIg and IIIh and:
Y is hydrogen;
$Y^1$ and $Y^2$ are (i) independently hydrogen, $C_{1-6}$-alkyl, $C_{2-6}$-alkenyl, $C_{1-6}$-alkylthio, phenyl, phenylthio, or (ii) $Y^1$ and $Y^2$ taken together with the carbon to which they are attached are VIa wherein G is hydrogen or phenyl;
$Y^3$ is hydrogen;
$Y^4$ and $Y^5$ independently of each are hydrogen, $C_{1-6}$-alkyl, aryl or arylthio.

6. A process according to claim 2 wherein the ruthenium (II) carbine complex is IIIb and:
$R^b$ is $C_{1-6}$-alkyl or $C_{1-6}$ haloalkyl;
a, b and d are hydrogen and c is hydrogen, halogen, nitro, $C_{1-6}$-alkylcarbonyl amino, aryl carbonyl amino, aryl sulfonyl amino, alkyl sulfonyl amino, $C_{1-6}$ haloalkyl sulfonyl amino, $SO_2$—NR'R" wherein R' and R" (i) independently of each other are hydrogen, $C_{1-6}$-alkyl or aryl or (ii) R' and R" together with the N to which they are attached form a carbocycle.

7. A process of claim 2 wherein the ruthenium(II) carbine complex is IIIe and Arene is benzene, p-cymene, mesitylene or, p-xylene.

8. A process according to claim 2 wherein the ruthenium (II) carbine complex is IIId and $R^{2a}$ is $C_{1-6}$-alkyl.

9. A process according to claim 2 wherein the ring closing metathesis reaction in step (a) is performed in an organic solvent at 20° C. to 140° C.

10. A process according to claim 2 wherein the ring closing metathesis reaction in step (a) is performed with a substrate to catalyst ratio in the range of 20 to 10000.

11. A process according to claim 2 wherein the ring closing metathesis reaction in step (a) is performed with a substrate concentration in the range of 0.1 and 25%.

12. A process according to claim 1 wherein the macrocyclic acid of formula XX obtained in step (b) is isolated by way of extraction with dichloromethane and a subsequent crystallization in tetrahydrofuran.

13. A process according to claim 1 wherein the macrocyclic acid of formula XX is obtained without isolation of the macrocyclic ester of formula I.

14. A process according to claim 1 further comprising treating XX wherein $R^1$ is an amino protecting group and X is halogen with acetic acid anhydride in the presence of an inorganic base and a suitable organic solvent to afford an azlacton intermediate of formula XXIII

XXIII which is treated with cyclopropyl sulfonamide in the presence of an inorganic base afford a compound of formula XXI.

15. A process according to claim 1 wherein the sodium base in step (d) is sodium hydroxide, sodium methylate or sodium ethoxide.

16. A process according to claim 1 wherein the PG is $C_{1-6}$-alkylcarbonyl, arylcarbonyl or $C_{1-6}$-alkoxycarbonyl.

17. A process according to claim 16 wherein the PG is benzoyl.

18. A process according to claim 1 wherein $R^1$ is Boc, $R^2$ is ethyl and the moiety and the moiety XXIVa is XXIVb:

XXIVa

XXIVb

19. A compound of formula I wherein:

(I)

wherein $R^4$ and PG are amino protecting groups, $R^5$ is $C_{1-4}$-alkyl and X is halogen.

20. A compound according to claim 19 wherein $R^4$ is Boc, $R^5$ is ethyl, PG is $C_{1-6}$-alkylcarbonyl, arylcarbonyl or $C_{1-6}$-alkoxycarbonyl and the moiety XXIVa is XXIVb:

XXIVa

XXIVb

21. A compound according to claim 20 wherein PG is benzoyl.

22. A compound of formula II wherein;
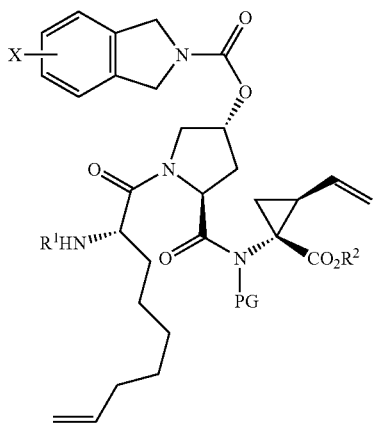
II
R¹ and PG are amino protecting groups, R² is $C_{1-4}$-alkyl and is X is halogen.
23. A compound according to claim 22 wherein R¹ is Boc; R² is ethyl; PG is $C_{1-6}$-alkylcarbonyl, arylcarbonyl or $C_{1-6}$-alkoxycarbonyl and the moiety XXIVa is XXIVb:
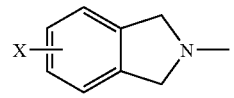
XXIVa
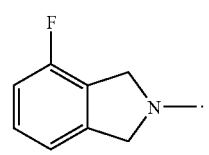
XXIVb
24. A compound according to claim 23 wherein PG is benzoyl.
* * * * *